(12) United States Patent
Baxi et al.

(10) Patent No.: US 10,485,433 B2
(45) Date of Patent: Nov. 26, 2019

(54) RELIABLE ESTIMATION OF PULSE TRANSIT TIME IN MOTION FOR CUFFLESS BLOOD PRESSURE ESTIMATION

(71) Applicant: Intel Corporation, Santa Clara, CA (US)

(72) Inventors: Amit S. Baxi, Thane (IN); Vincent S. Mageshkumar, Navi Mumba (IN)

(73) Assignee: Intel Corporation, Santa Clara, CA (US)

( * ) Notice: Subject to any disclaimer, the term of this patent is extended or adjusted under 35 U.S.C. 154(b) by 386 days.

(21) Appl. No.: 15/394,702

(22) Filed: Dec. 29, 2016

(65) Prior Publication Data

US 2018/0184921 A1    Jul. 5, 2018

(51) Int. Cl.
*A61B 5/021* (2006.01)
*A61B 5/0456* (2006.01)
*A61B 5/04* (2006.01)
*A61B 5/00* (2006.01)
*A61B 5/024* (2006.01)

(52) U.S. Cl.
CPC ...... *A61B 5/02125* (2013.01); *A61B 5/04012* (2013.01); *A61B 5/0456* (2013.01); *A61B 5/6802* (2013.01); *A61B 5/7278* (2013.01); *A61B 5/02416* (2013.01)

(58) Field of Classification Search
CPC ............ A61B 5/02125; A61B 5/02416; A61B 5/04012; A61B 5/0456; A61B 5/6802; A61B 5/7278
USPC .......................................................... 600/480
See application file for complete search history.

(56) References Cited

U.S. PATENT DOCUMENTS

| | | |
|---|---|---|
| 7,881,790 B1 | 2/2011 | Turcott |
| 2004/0015091 A1 | 1/2004 | Greenwald et al. |
| 2013/0310660 A1 | 11/2013 | Zuckerman-Stark et al. |
| 2015/0313486 A1* | 11/2015 | Mestha ............... A61B 5/02125 600/301 |

(Continued)

FOREIGN PATENT DOCUMENTS

WO    PCTUS2016040476    6/2016

OTHER PUBLICATIONS

International Search Report and Written Opinion for PCT Patent Application No. PCT/US17/61304, dated Jan. 25, 2018, 11 pages.

*Primary Examiner* — Michael J Carey
(74) *Attorney, Agent, or Firm* — Compass IP Law, PC

(57) ABSTRACT

Apparatuses, systems, and methods described herein can enable reliable estimation of pulse transit time (PTT) for a user in motion for cuffless blood pressure estimation. In one embodiment, a method involves receiving an electrocardiographic (ECG) signal and a photoplethysmographic (PPG) signal and detecting R-wave peaks in the ECG signal. The method further involves identifying multiple segments of the PPG signal based on detection of the R-wave peaks of the ECG signal, wherein a given segment of the PPG signal comprises multiple samples and is aligned with a corresponding R-wave. The method also involves generating an averaged PPG wave based on the multiple segments of the PPG signal, wherein a given element of the averaged PPG wave comprises an average of corresponding elements from the multiple segments of the PPG signal, and computing the blood pressure value based on the averaged PPG wave.

20 Claims, 14 Drawing Sheets

(56) References Cited

U.S. PATENT DOCUMENTS

2016/0089047 A1 3/2016 Jonnada et al.
2016/0157782 A1 6/2016 Kumar et al.
2016/0360986 A1* 12/2016 Lange .................. A61B 5/6829

* cited by examiner

RELIABLE ESTIMATION OF PULSE TRANSIT TIME IN MOTION FOR CUFFLESS BLOOD PRESSURE ESTIMATION

FIELD

The descriptions are generally related to sensing one or more biological functions, and more specifically, pulse transmit time estimation for cuffless blood pressure estimation.

COPYRIGHT NOTICE/PERMISSION

Portions of the disclosure of this patent document may contain material that is subject to copyright protection. The copyright owner has no objection to the reproduction by anyone of the patent document or the patent disclosure as it appears in the Patent and Trademark Office patent file or records, but otherwise reserves all copyright rights whatsoever. The copyright notice applies to all data as described below, and in the accompanying drawings hereto, as well as to any software described below: Copyright© 2016, Intel Corporation, All Rights Reserved.

BACKGROUND

Advances in computing technologies and sensor devices encourages the incorporation of more technology in wearable sensors and personal computing systems. Such technologies offer the hope of obtaining biometric data from devices that are small and unobtrusive enough to be carried and/or worn. Biometric data has particular interest in health and well-being monitoring, as well as sports performance monitoring. However, there are traditionally many limitations encountered in designing and implementing actual systems that generate usable biometric data.

For example, data obtained with a wearable sensor when a user is in motion (e.g., walking or during other forms of motion) can include significant motion artifacts. Motion artifacts can be significant enough to cause inaccuracies in the data collected with the sensor.

BRIEF DESCRIPTION OF THE DRAWINGS

The following description includes discussion of figures having illustrations given by way of example of implementations of embodiments of the invention. The drawings should be understood by way of example, and not by way of limitation. As used herein, references to one or more "embodiments" are to be understood as describing at least one implementation of the invention that includes one or more particular features, structures, or characteristics. Thus, phrases such as "in one embodiment" or "in an alternate embodiment" appearing herein describe various embodiments and implementations of the invention, and do not necessarily all refer to the same embodiment. However, they are also not necessarily mutually exclusive.

Descriptions of certain details and implementations follow, including a description of the figures, which may depict some or all of the embodiments described below, as well as discussing other potential embodiments or implementations of the inventive concepts presented herein.

DETAILED DESCRIPTION

Methods, apparatuses, and systems for estimation of pulse transit time for cuffless blood pressure measurement are described. "Cuffless" blood pressure measurement refers to blood pressure measurement without relying on a traditional blood pressure cuff. Typically, techniques for cuffless blood pressure measurement are ineffective when a user is in motion (e.g., walking or in the presence of other motion). In contrast, embodiments described herein can enable accurate determination of PTT and a blood pressure value without requiring a traditional blood pressure cuff and in the presence of significant motion noise.

In one embodiment, a method of measuring blood pressure involves receiving an electrocardiographic (ECG) signal and a photoplethysmographic (PPG) signal and detecting R-wave peaks in the ECG signal. The method also involves identifying multiple segments of the PPG signal based on the detected R-wave peaks of the ECG signal. In one such example, a given segment of the PPG signal has multiple PPG samples and is aligned with a corresponding detected R-wave peak. An average PPG waveform can then be generated by computing an average of corresponding samples from the multiple segments. Blood pressure can then be computed based on the averaged PPG wave. In one such embodiment, by using the R-wave peaks of the ECG signal to select segments from the PPG signal for averaging, an accurate blood pressure can be determined without a cuff and in the presence of motion noise.

Figure 1:
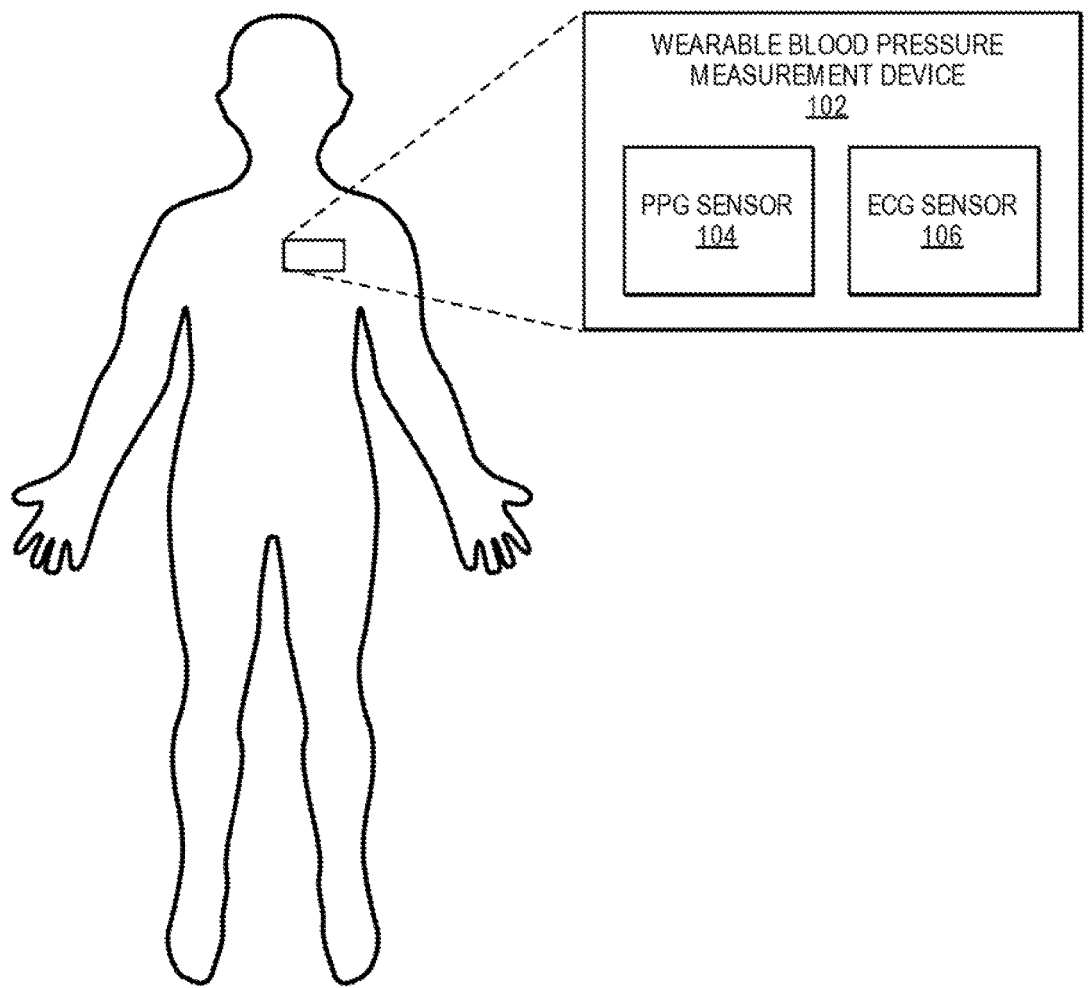
FIG. 1 illustrates a wearable blood pressure measurement device on a user, in accordance with embodiments.

FIG. 1 illustrates a wearable blood pressure measurement device on a user, in accordance with embodiments. In one embodiment, the wearable blood pressure measurement device 102 is a wearable flexible patch platform for determining a blood pressure value of a user. Unlike existing blood pressure measurement devices that require the use of a blood pressure cuff, the wearable blood pressure patch is a "cuffless" solution in that a user can use the patch without a blood pressure cuff to obtain a blood pressure reading. The wearable blood pressure measurement device 102 includes an adhesive to adhere to a user's skin in the torso region. Thus, the wearable blood pressure measurement device 102 includes sensors and circuitry to determine a blood pressure value based on sensors attached to a user's torso without relying on a cuff, in accordance with embodiments.

In one embodiment, the wearable blood pressure patch estimates blood pressure based on a photoplethysmographic (PPG) signal and an electrocardiographic (ECG) signal (or electrokardiogram (EKG) signal). For example, in the illustrated embodiment, the wearable blood pressure measurement device 102 includes PPG sensor 104 and an ECG sensor 106. The PPG sensor 104 can include a light source such as light emitting diodes (LEDS) to illuminate the skin and optical sensors such as photodiodes to detect light reflected back to the PPG sensor. Blood in the arteries causes the arteries to expand and contract as blood from the heart is transported to and away from the arteries, respectively. An expanded artery in proximity to the light sensor will typically reflect more light back to the sensor than the same artery that is not expanded. This difference in reflected light can be used to determine blood flow conditions in the arteries, in accordance with embodiments. In one embodiment, the ECG sensor includes electrodes (e.g., electrically conductive elements) to detect electrical activity of the heart through the user's skin.

Based on the PPG and ECG signals, circuitry on the wearable blood pressure patch can determine a pulse transit time (PTT). PTT is a measurement of the time it takes for a pulse of blood to travel from the heart to a peripheral location on the body. PTT is inversely correlated to BP. Accordingly, circuitry on the wearable blood pressure patch can use signals from the ECG and PPG sensors to determine PTT, and based on the PTT, estimate a blood pressure value.

Figure 2:
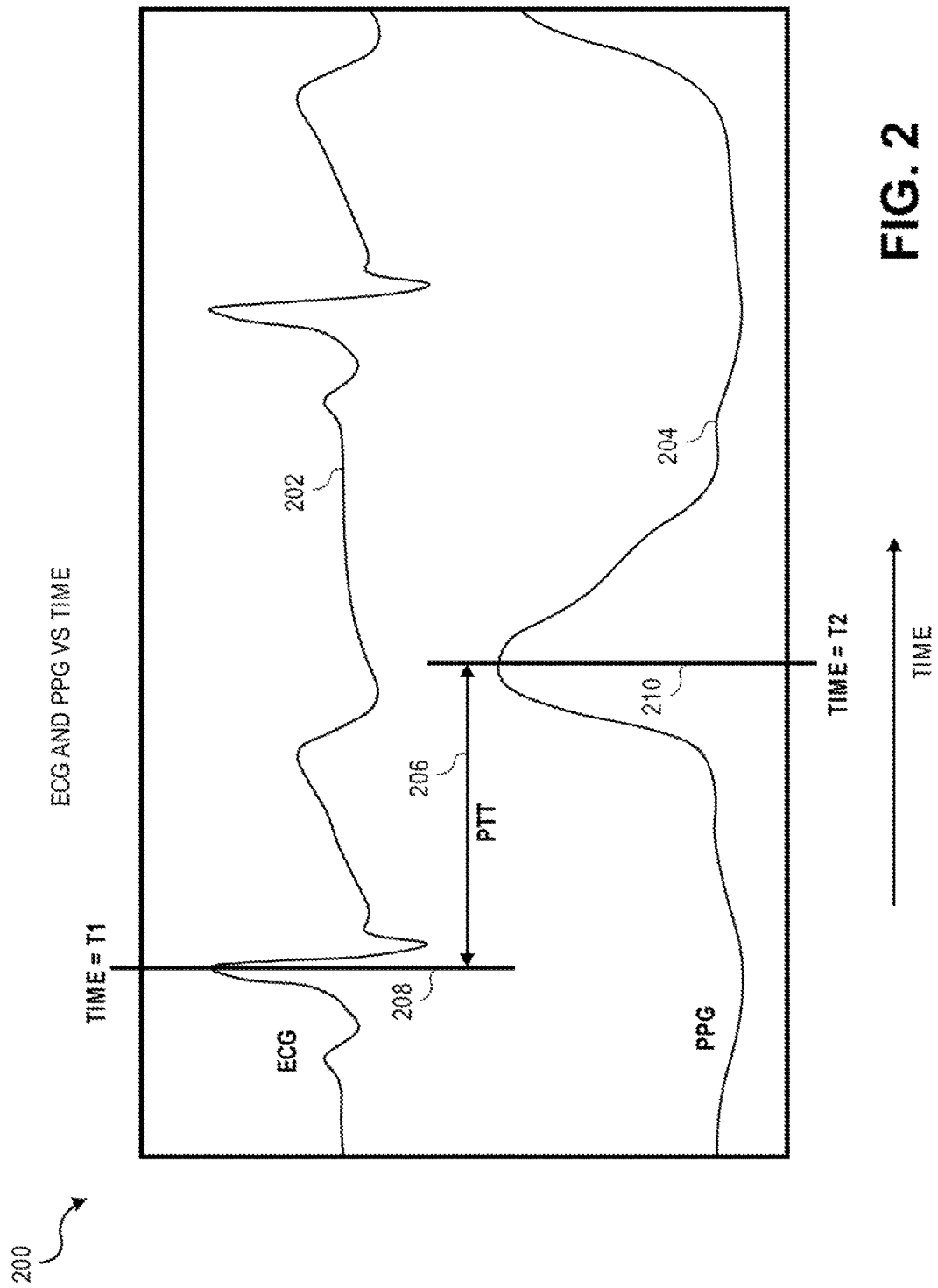
FIG. 2 illustrates a graph of an electrocardiographic (ECG) signal and a photoplethysmographic (PPG) signal versus time, in accordance with embodiments.

FIG. 2 illustrates a graph 200 of an electrocardiographic (ECG) signal and a photoplethysmographic (PPG) signal versus time, in accordance with embodiments. The line 202 corresponds to the ECG waveform and the line 204 corresponds to the PPG waveform. The PTT 206 is measured between a peak of the ECG waveform and a corresponding peak of the PPG waveform. In the illustrated example, the peak of the ECG waveform occurs at time T1, the time corresponding to line 208. The peak of the PPG waveform occurs at time T2, the time corresponding to the line 210. Thus, the PTT 206 is the time between the peaks 208 and 210.

The accuracy of blood pressure estimation from PTT depends on the accuracy of the PTT measurement. A typical PTT value at rest is about 200 milliseconds (ms). An error of even 1 ms in the PTT measurement can translate to 1 mmHg error in the blood pressure estimate. In accordance with embodiments, the maximum permissible error is 5 mmHg. Thus, in accordance with embodiments, an error of more than 5 ms in the PTT measurement causes an unacceptably high error in the blood pressure estimate. Therefore, accurate PTT measurement can be critical for blood pressure estimation based on PTT. Unfortunately, existing systems to measure blood pressure based on PTT are not sufficiently accurate when a user is in motion (e.g., due to inaccurate PPG or ECG measurements). Typically, the motion of a user causes more errors in PPG measurements than in ECG measurements.

Figure 3:
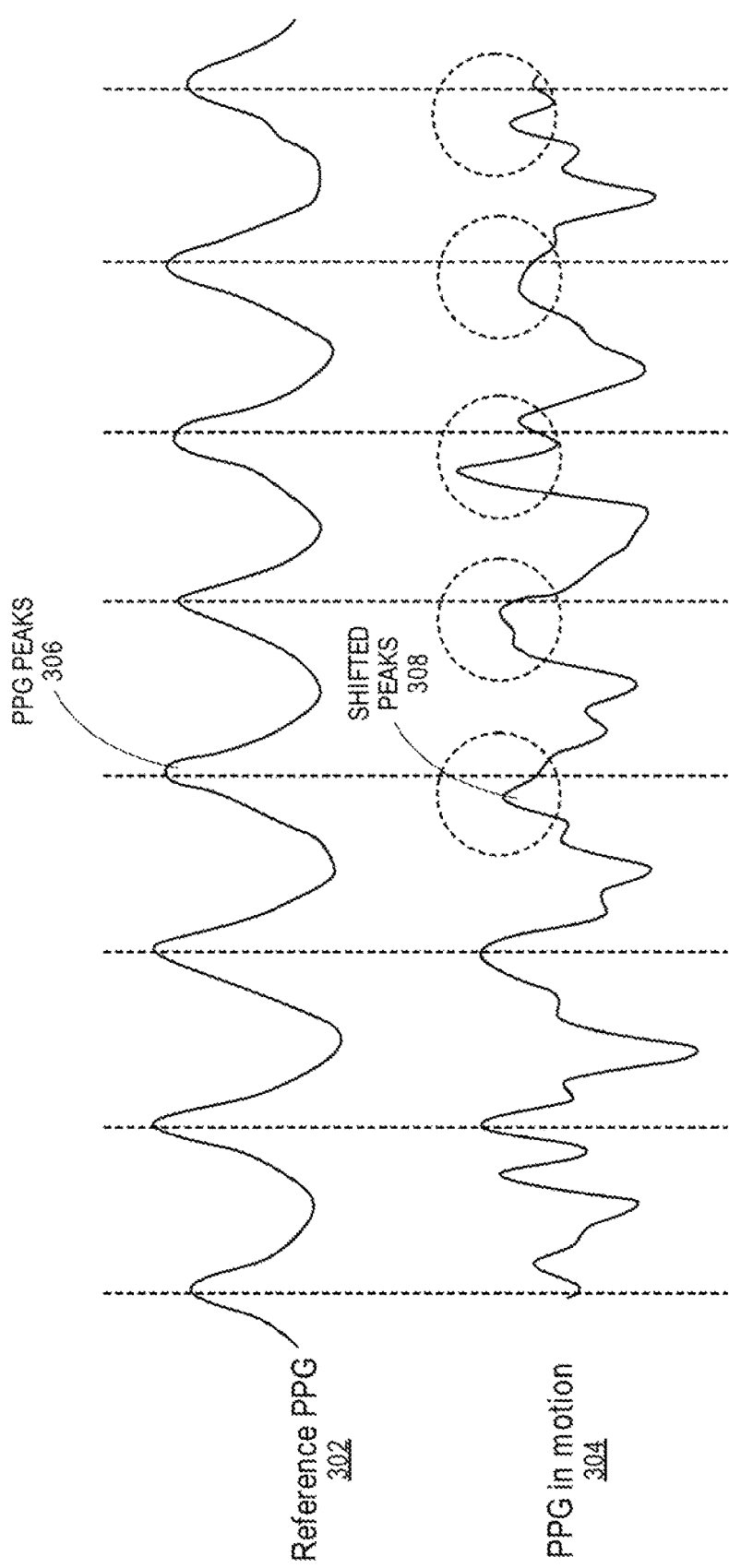
FIG. 3 illustrates PPG waveforms for a user at rest and while walking, in accordance with embodiments.

For example, FIG. 3 illustrates PPG waveforms for a user at rest and while walking, in accordance with embodiments. FIG. 3 includes a reference PPG waveform 302, and a PPG waveform 304 for a user in motion. The vertical dotted lines indicate the location of PPG peaks 306 on the reference PPG waveform 302.

As illustrated in FIG. 3, the reference PPG waveform 302 for a user at rest is free from noise, and the PPG peaks are easily identifiable. In contrast, the PPG waveform 304 for a user in motion has a significant amount of motion noise. Due to additive motion noise, the PPG peaks can become shifted by up to 50 ms in some cases (see, for example, the shifted peaks 308), or masked. Motion noise can cause PPG peaks to shift by an amount that is significant enough to cause an unacceptably high error rate in the resulting PTT and blood pressure estimations. PPG measurements are typically more susceptible to motion noise when compared to ECG measurements due to the nature of the sensor used to obtain the PPG signal. For example, a PPG sensor can include LEDs and photodiodes that touch the skin, but can move slightly when the user moves (unlike ECG sensor electrodes, for example, which are typically securely adhered to a user's skin and experience less movement). Furthermore, existing techniques are not able to extract a PPG signal in the presence of motion noise because the frequency components of the motion noise can completely overlap the PPG signal spectrum. As a result, traditional signal processing techniques are ineffective at filtering out the noise and identifying the true PPG peaks. For example, traditional signal processing techniques such as digital bandpass filters for reducing noise frequencies are ineffective because the filters also eliminate PPG signal components due to the spectral overlap between the noise and PPG signal. Similarly, threshold based techniques are ineffective for peak detection because signal peaks can be completely masked or shifted due to spurious noise peaks. Therefore, existing devices that use PPG to estimate blood pressure are ineffective when the user is in motion.

In contrast, embodiments include techniques for accurately determining PTT, and therefore accurately determining blood pressure, by identifying true PPG peaks in the presence of severe motion artifacts. In one embodiment, a method of determining a blood pressure value involves receiving an ECG and a PPG signal and detecting R-wave peaks in the ECG signal. The method further involves identifying multiple segments of the PPG signal based on detection of the R-wave peaks of the ECG signal, wherein a given segment is aligned with a corresponding R-wave peak. For example, the R-waves of the ECG signal can act as anchor points to determine segments of the PPG signal to average. The method then involves computing an average of corresponding samples from multiple segments to generate an averaged PPG wave. Finally, the blood pressure value can be computed based on a PTT measurement, which can be based on the averaged PPG wave.

Figure 4:
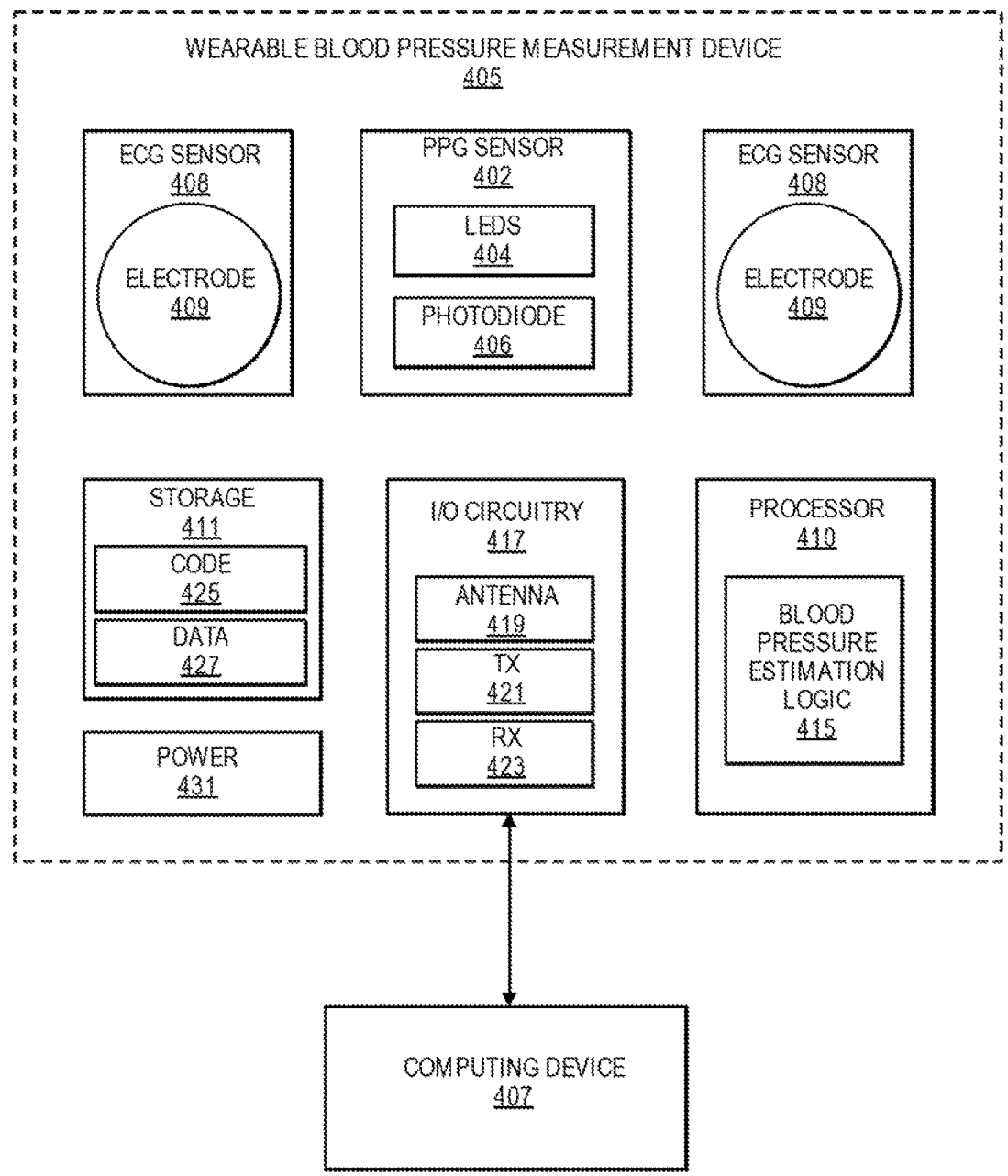
FIG. 4 illustrates a block diagram of a blood pressure measurement system, in accordance with embodiments.

FIG. 4 illustrates a block diagram of a blood pressure measurement system, in accordance with an embodiment. The system in FIG. 4 illustrates an embodiment of a wearable device 405 for measuring blood pressure without a blood pressure cuff. The wearable blood pressure measurement device 405 is an example of the device 102 of FIG. 1 that can be worn by a user to measure blood pressure both at rest and in motion. The wearable blood pressure measurement device 405 includes a patch with sensors for detecting ECG and PPG signals and other circuitry for measuring biologic signals, in accordance with embodiments.

In the illustrated embodiment, the wearable blood pressure measurement device 405 includes an ECG sensor 408 and a PPG sensor 402. The ECG sensor 408 includes a plurality of conductive electrodes 409. The conductive electrodes 409 can include a metal such as copper, gold, silver, aluminum, tin, titanium, platinum, nickel, a combination of metals, or another conductive material. In one embodiment, the ECG electrodes 409 are dry conductive electrodes, as compared to conventional ECG electrodes with jelly (which can result in a progressively deteriorating signal over time).

The illustrated embodiment also includes a PPG sensor 402 for detecting a PPG signal as described above. In the illustrated embodiment, the PPG sensor 402 includes one or more light emitting diodes (LEDs) 404 and one or more photodiodes 406. The LEDs 404 produce light. The light is emanated to blood of the user wearing the device 405 and is reflected and scattered, at least partially, by the blood back to the photodiode 406. In one or more embodiments, the LEDs produce light in the visible spectrum (e.g., green or another color of light that is suitable for detecting a PPG signal). The photodiode 406 detects changes in light reflected from the skin. For example, the pulsatile blood flow changes the intensity of reflected light. Different amounts of light are reflected depending on a state of blood flow near the skin. In one or more embodiments, a red and an infra-red LED can be used in conjunction with a green LED to help provide real-time, ambulatory monitoring of blood oxygen saturation.

In the illustrated embodiment, the wearable blood pressure measurement device 405 also includes a processor 410, input/output (I/O) circuitry 417, and storage 411. The processor 410 can includes any processing device or computational circuit, such as a microprocessor (e.g., including one or more cores), a microcontroller, a digital signal processor (DSP), or any other type of processor or processing device. In accordance with embodiments, processor 410 receives signals from the PPG sensor 402 and ECG sensor 408 via conductive interconnects and performs computations using the data received from the sensors. The processor 410 can store data 427 from the sensors, computed values, or both in a storage device 411. The storage device 411 can include one or more types of electronic storage, such as volatile memory, nonvolatile memory, or both to store data, code, or other information such as computed PTT or blood pressure measurements. Volatile memory is memory whose state (and therefore the data stored on it) is indeterminate if power is interrupted to the device. Nonvolatile memory refers to memory whose state is determinate even if power is interrupted to the device. Other embodiments include no or minimal storage and instead transmit data (e.g., averaged PPG values, PTT values, blood pressure values) to an external computing device 407 rather than storing data locally. Other embodiments can both store data in storage 411 and transmit data to an external computing device either at predetermined intervals, on demand, or can stream data real time to an external computing device 407. The external computing device can include a mobile device or other computing device, such as the computing devices described below with respect to FIGS. 12 and 13. The device 405 also includes a power source 431 to provide power to the components of the device 405. For example, the power source 431 can include an internal battery or other power source.

In the illustrated embodiment, the wearable blood pressure measurement device 405 includes I/O circuitry 417 to interface with the external computing device 407. The I/O circuitry 417 can include circuitry for coupling the wearable blood pressure measurement device 405 with the external computing device 407. The I/O circuitry can also include circuitry for receiving signals from sensors on the device 405, such as a PPG and ECG signal. As used herein, coupling can refer to an electrical coupling, communicative coupling, physical coupling, or a combination of these. Physical coupling can include direct contact. Electrical coupling includes an interface or interconnection that allows electrical flow between components, or allows signaling between components, or both. Communicative coupling includes connections, including wired or wireless, that enable components to exchange data. In one embodiment, the I/O circuitry includes wireless transmission circuitry such as transmission circuitry 421 to provide modulated radio signals to an antenna 419 for transmitting wireless signals (e.g., Bluetooth®, induction wireless, infrared wireless, ultra-wideband, ZigBee, or other personal area network compliant signals). The I/O circuitry 417 can also include receiving circuitry 423 to receive signals from the external computing device 407. The I/O circuitry 417 can also, or alternatively include wires within an integrated circuit interface to couple with a pad, pin, or connector to interface signal lines or traces or other wires between devices. I/O interface circuitry 417 can include drivers, receivers, transceivers, or termination, or other circuitry or combinations of circuitry to enable the transmission and receipt of signals between devices.

Referring again to the processor 410, the processor can execute blood pressure estimation logic 415 to determine a blood pressure value based on the data received from the ECG sensor 408 and the PPG sensor 402. The blood pressure estimation logic 415 can include software, hardware, or a combination of software and hardware to perform methods of determining a blood pressure value and described herein. Note that although the blood pressure estimation logic 415 is illustrated in FIG. 4 as being in the processor 410, in one embodiment in which the blood pressure estimation logic 415 includes hardware logic to perform one or more operations, such hardware logic can be external to the processor 410. In one embodiment, program code 425 for performing a method of determining a blood pressure value is stored in storage 411. The processor 410 can execute the code 425 to perform a method in accordance with an embodiment described herein. Note that although the example in FIG. 4 is referred to as a "blood pressure" measuring device, in other embodiments, the measurement of PPG and ECG signals, the computation of PTT, and blood pressure estimation can be performed by different devices. For example, in one embodiment, a wearable device detects and transmits PPG and ECG values, and an external device receives the signals and determines a blood pressure value based on the received signals.

Figure 5:
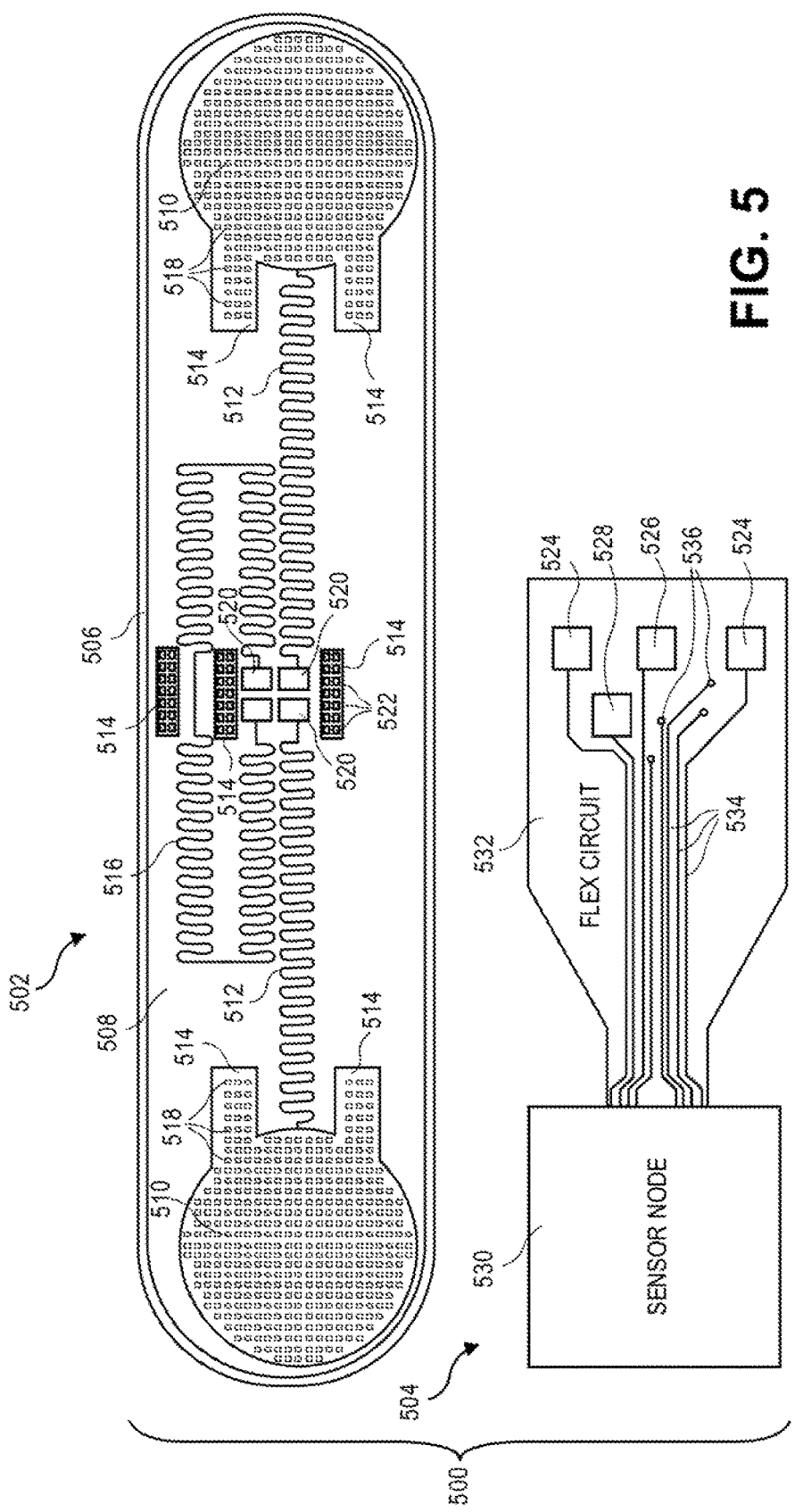
FIG. 5 illustrates one example of a wearable blood pressure measurement device, in accordance with an embodiment.

FIG. 5 illustrates one example of a wearable blood pressure measurement device in accordance with an embodiment. The wearable blood pressure measurement device 500 can be the same or similar to the device 405 of FIG. 4. The system 500 as illustrated includes a flexible, stretchable patch 502 and a control circuit 504. The view provided in FIG. 5 shows the side of the patch that faces the surface of a user's skin that is wearing the patch. The patch 502 can include a flexible, stretchable material to enable a user to wear the patch 502 in a torso region at rest or in motion. A material is "flexible" if the material can rotate and bend, and a material is "stretchable" if the material can lengthen in response to an applied force such as pulling. In one embodiment, the patch 502 includes a flexible, stretchable substrate 508 onto which the circuitry is disposed. The substrate 508 can also be attached to or on a flexible, stretchable support material 506 such as a fabric. The fabric 506 can include a material used in clothing, such as Lycra, vinyl, polyamide polyurethane-elastane, velvet, cotton, denim, polyester, or another flexible, stretchable fabric. The fabric 506 can provide mechanical strength for the substrate 508 and circuitry on the substrate. For example, the fabric 506 can enable the patch 502 to withstand more force in being stretched, bent, rotated, or otherwise having force exerted thereon.

In accordance with embodiments, the substrate 508 can include a flexible, stretchable material, such as thermoplastic polyurethane (TPU), silicone and/or polydimethylsiloxane (PDMS), poly (lactic acid) based polymers or co-polymers, other bio-compatible tri-block copolymers, thermosets (e.g., polyuria), polydimethylsiloxane (PDMS), or another flexible, stretchable material over which circuitry can be disposed. The substrate 508 can be attached to the fabric 506 (when present) by heat pressing the substrate 508 into the fabric 506, or by another means of attaching the substrate to the fabric.

A first metallization layer can be situated on the substrate 508, such as by an additive process (e.g., printing, deposition, or another additive process), a subtractive process (e.g., a process that includes removing material, such as by etching), or both. In the illustrated embodiment, the first metallization on the substrate material 508 includes a plurality of ECG electrodes 510, meandering traces 512, stretch limiting patches 514, a stretch sensor 516, and contact pads 520 (note that not all contact pads include reference numerals so as to not obscure the view of other portions of the patch 502). The first metallization can include copper, gold, silver, aluminum, tin, titanium, palladium, platinum, nickel, a combination thereof, or another conductive material. The ECG electrodes 510, meandering traces 512, stretch limiting patches 514, stretch sensor 516, and the pads 520 can be made of different or same materials.

In one embodiment, the ECG electrodes 510 are dry conductive electrodes, such as the electrodes 409 described above with respect to FIG. 4. The ECG electrodes 510 can include perforations 518. The perforations 518 are voids in the electrodes 510. The perforations 518 can aid in anchoring the electrodes 510 to the substrate 508. The perforations 518 can also help reduce overall cost of the device, such as when using an additive manufacturing technique (e.g., conductive ink printing). For example, an inkjet process can use a silver-based printing material (e.g., a silver-based conductive "ink") to form the ECG electrodes as well as other metal features. The perforations 518 can also help increase flexibility without significantly impacting performance (e.g., electrical performance characteristics) of the electrode 510.

The traces 512 electrically couple the electrodes 510 to respective pads 520. In the illustrated embodiment, the traces 512 are formed with a meandering pattern, such as to increase the stretchability, flexibility, or both of the patch 502 as compared to using generally straight traces. The stretch limiting patches 514 can include metallization with perforations 522 similar to the perforations 518. The stretch limiting patches 514 are positioned to help prevent breakage of other metallization, such as the electrodes 510, electrical junctions between the traces 512 and other metallization, pads 520, or the interconnect between the fabric 506 and the substrate 508. The stretch limiting patches 514 constrain the strain in the regions in and around the stretch limiting patches and help prevent over-stretching in areas that might otherwise break if the patch 502 is over-stretched. The ECG electrodes 510 can be low-profile, thin, stretchable, flexible, low-cost, disposable, or a combination of those properties.

The stretch sensor 516 can provide, by way of resistance measurements, an indication of an amount to which the stretch sensor 516 is stretched. The resistance value of the meandering traces of the stretch sensor 516 can change as they are stretched more or less. Circuitry that is connected to the pads 520 that are electrically connected to the stretch sensor 516 can determine the resistance. The circuitry can interpret, modify, or otherwise analyze the resistance to determine a respiration rate and/or heart rate of the individual wearing the system 500.

The control circuit 504 as illustrated includes a sensor node 530 and a flex circuit 532. The flex circuit 532 can be electrically and mechanically coupled to the sensor node 530. For example, in the illustrated embodiment, the traces 534 provide a conductive path to the sensor node 530. The vias 536 provide a path for signals to travel from one layer of the flex circuit 532 to another layer of the flex circuit 532. The sensor node 530 can include electronic components (e.g., an oscillator, resistors, transistors, processors, switches, inductors, capacitors, diodes, amplifiers, voltage and/or current regulators, voltage and/or current boosters, antennas, power sources (e.g., batteries), or other electronic components. In one embodiment, the sensor node 530 includes circuitry and logic to process, store, and transmit data such as PPG, ECG, PTT, and blood pressure values. For example, the sensor node 530 can include one or more of processing circuitry, I/O circuitry, and storage in accordance with FIG. 4. The flex circuit 532 as illustrated includes a plurality of light emitting diodes (LEDs) 524, a photodiode 526, a sensor 528, traces 534, and vias 536. While not shown in this view of the flex circuit 532, the flex circuit 532 can include one or more contact pads to couple the flex circuit 532 with the patch 502. The flex circuit 532, in one or more embodiments includes a polyimide substrate with second metallization (e.g., second traces 534 or other metallization) therein or thereon. The second metallization can include the second traces 534, vias, and/or second pads, such as can be used to mount the flex circuit 532 on the patch 502 or to mount one or more of the LEDs 524, photodiode 526, and sensor 528 on the flex circuit 532. Signals from the ECG electrodes 510 and/or the stretch sensor 516 can be provided to the sensor node 530 through second metallization on the flex circuit 532.

The LEDs 524 and photodiode 526 can be in accordance with the LEDs 404 and photodiode 406 of FIG. 4, and can enable detection of a PPG signal. In one or more embodiments, the LEDs 524 can be low-profile screen printed/organic LEDs. The system 500 can also include other sensors, such as a temperature detector (TD) (e.g., a thermistor, a resistance thermometer, or a resistance TD (RTD)), a motion sensor, noise sensor, or mechanical sensor. An RTD is a component that changes resistance with temperature in a predictable manner. RTDs are typically made from a pure metal, such as copper, nickel, or platinum, wrapped in a coil around a core, such as a ceramic or glass. A motion sensor (sometimes referred to as an accelerometer) detects whether and/or a general direction of acceleration of the sensor. A noise sensor detects external electromagnetic signals and provides a signal indicative of a magnitude of the detected signals. The signals from one or more of the motion, noise, and stretch sensor can be used for adaptive noise cancellation and can help reduce motion related noise from bio-signals.

Unlike current ECG-only patches available in the market today the system 500 can integrate two or more of ECG electrodes, optical PPG sensors, temperature sensor (e.g., the thermistor 528), and respiration sensor (e.g., the stretch sensor 516) onto the same flexible substrate (e.g., a combination of the flex circuit 532, substrate material 508, and the fabric 506). Mounting the rigid LEDs 524 on a flexible polyimide (e.g., the substrate of the flex circuit 532) and then on the substrate 508 can help to improve reliability at rigid-flex junctions. This is at least in part due to the components being rigid and providing localized flex and stretch resistance near the components.

Figure 6:
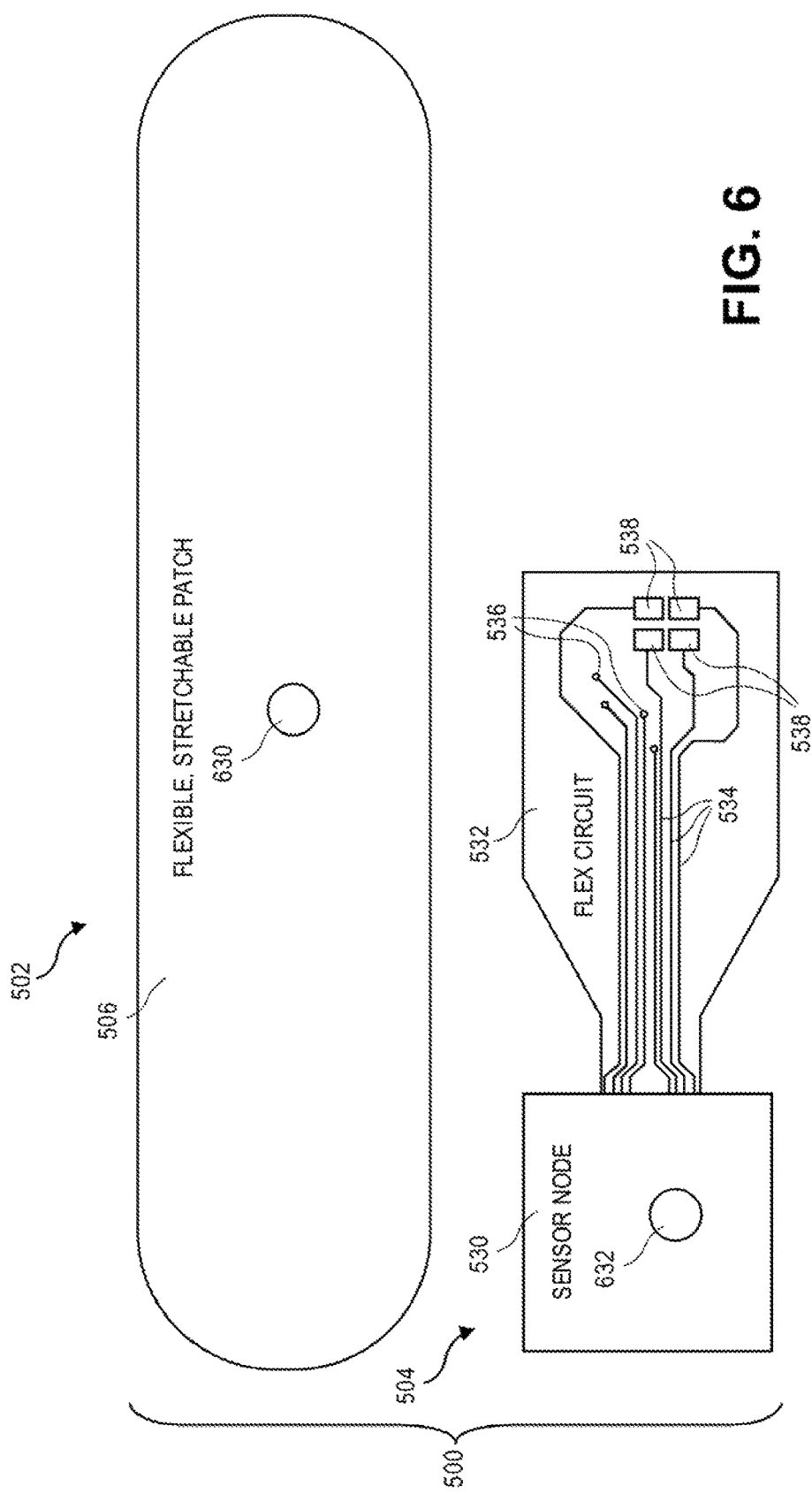
FIG. 6 illustrates another view of the embodiment of the system of FIG. 5, in accordance with embodiments.

FIG. 6 illustrates another view of the embodiment of the system 500 of FIG. 5, in accordance with embodiments. The view shown in FIG. 6 are the portions of the system 500 that are facing away from the user wearing patch (e.g., an external view).

The patch 502 in the illustrated embodiment includes an optional male or female connection feature 630. The sensor node 530 in the illustrated embodiment includes a mating female or male connection feature 632. The connection feature 630 can include a snap, magnet, connector, hook and loop, or other suitable connection feature. The connection feature 632 can include the mating snap, magnet, connector, Velcro, other suitable connection feature. When in contact, the connection features 630 and 632 can secure the sensor node 530 to the fabric 506, in accordance with embodiments. In some embodiments that do not include the connection features 630 and 632, a double-sided adhesive tape, glue, or other attachment mechanism can be used to secure the sensor node 530 to the fabric 506.

As discussed above, the flex circuit 532 as illustrated includes contact pads 538. The contact pads 538 can be situated to align with the contact pads 520. The contact pads 538 can be in electrical and mechanical contact (e.g., by solder or a conductive adhesive) with the contact pads 520, such as to provide electrical signals from the contact pads 520 (e.g., from the electrodes 510 or stretch sensor 516) to the flex circuit 532.

Figure 7:
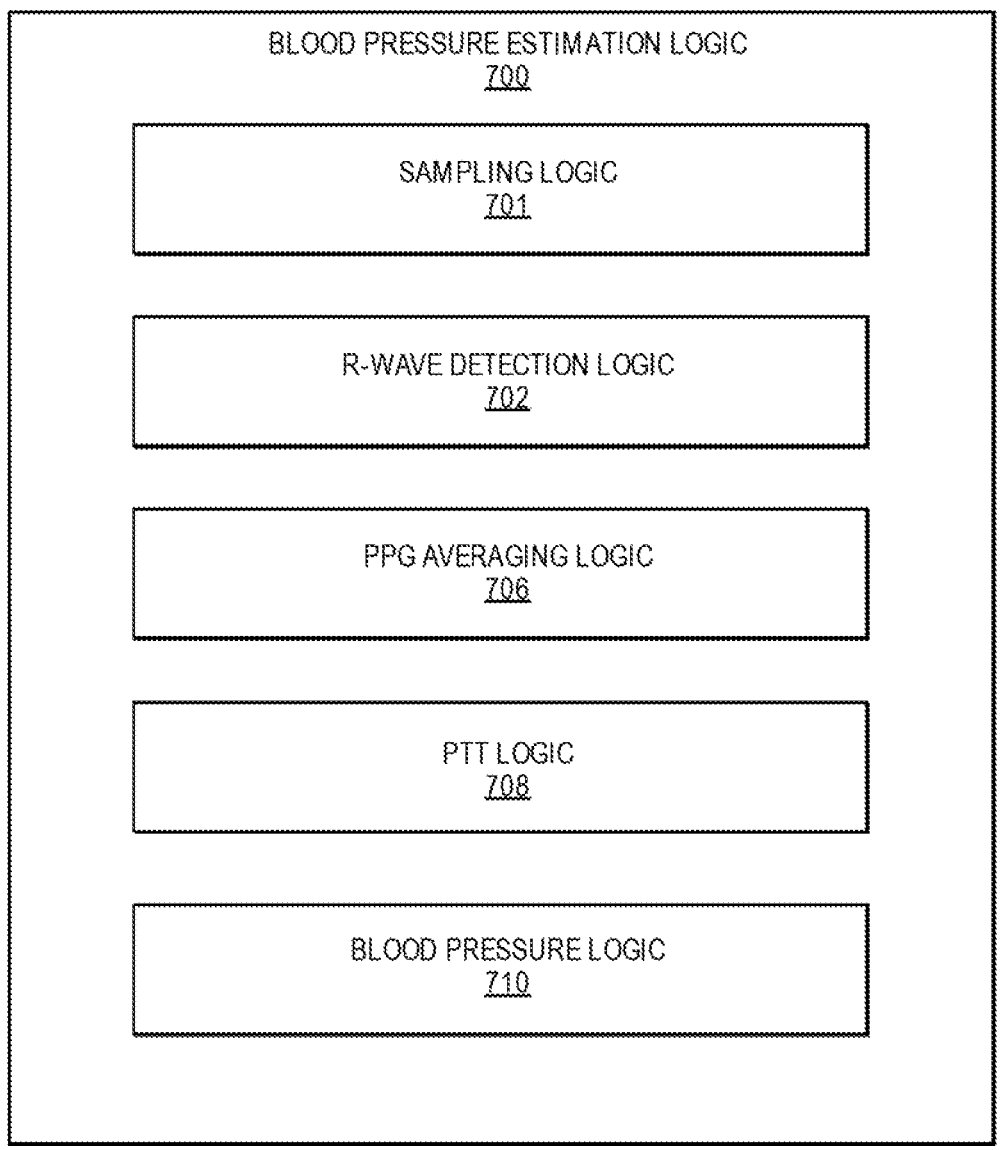
FIG. 7 is a block diagram of blood pressure estimation logic, in accordance with embodiments.

FIG. 7 is a block diagram of blood pressure estimation logic, in accordance with embodiments. The blood pressure estimation logic 700 is an example of the blood pressure estimation logic 415 of FIG. 4, in accordance with an embodiment. The blood pressure logic can include software, hardware, or a combination of software and hardware. The blood pressure estimation logic 700 of FIG. 7 includes logic to compute an accurate averaged PPG wave by using ECG R-waves as anchor points and logic to estimate blood pressure using the averaged PPG wave.

In the illustrated embodiment, the blood pressure estimation logic includes sampling logic 701. The sampling logic 701 can synchronously sample an ECG and PPG signal. Sampling involves the extraction of discrete samples from a continuous-time signal. A sample is a value (or a set of value) at a point in time. Thus, in one embodiment, the sampling logic 701 receives ECG and PPG signals from sensors attached to a user and extracts samples from the ECG and PPG signals over a sampling window. In on such embodiment, the sampling rate for the ECG and PPG signals is the same, which results in a same number of PPG samples as ECG samples for a given sampling window. In other embodiments, the sampling rate can be different (e.g., the sampling logic 701 can acquire more PPG samples or more ECG samples, in accordance with embodiments).

The blood pressure estimation logic 700 also includes R-wave detection logic 702. R-wave detection logic 702 includes logic to detect R-waves (e.g., R-wave peaks) in an ECG signal. FIG. 2 illustrates an example of an ECG signal 202 with an R-wave at time T1. The R-wave detection logic 702 takes a sampled ECG signal as an input and identifies a location of an R-wave peak. In one embodiment, the R-wave detection logic 702 can output a time or other indicator to indicate that an R-wave is detected in the ECG signal.

The blood pressure estimation logic 700 also includes PPG averaging logic 706. The PPG averaging logic 706 includes logic that computes an average PPG wave based on the ECG signal. As mentioned above, the PPG signal can be susceptible to motion noise, and filtering the motion noise can be impractical or impossible due to the spectral overlap between the noise and PPG signal. For example, one existing technique involves using a digital band pass filter in the time domain. Digital finite impulse response (FIR) and infinite impulse response (IIR) filters can be used for motion noise suppression for some signals. However, FIR and IIR filters are ineffective for de-noising PPG signals because the motion noise's frequency spectrum overlaps the PPG spectrum. Therefore, aggressive filtering can eliminate the PPG signal itself.

In another example, a technique uses spectrum subtraction in the frequency domain to suppress motion noise for some signals. Spectrum subtraction in the frequency domain typically relies on signal processing in the frequency domain. Specifically, spectrum subtraction involves subtraction of isolated band pass filtered noise signal frequencies from the PPG signal frequencies, and then the resultant frequencies are de-convoluted back in the time domain. Spectrum subtraction is not only computation intensive, but also ineffective due to significant overlap in the noise and PPG signal frequencies. The de-convoluted PPG waveform in the time domain often has the true PPG peaks missing as a result of the processing.

In yet another example, a technique using adaptive motion noise cancellation can be used to suppress motion noise in some signals. Adaptive motion noise cancellation relies on integrating a motion sensor (such as an accelerometer, an inertial measurement unit, a piezoelectric element, or gyroscope) in hardware in close proximity to optical PPG sensors. The motion noise measured by the motion sensors is fed to a proprietary noise model, which first tries to approximate measured motion noise and fit it to the actual motion noise induced in the PPG signal and then adaptively subtract the modeled motion noise from the signals using least squares approximation. Adaptive motion noise cancellation typically requires a separate motion sensor in hardware and is also computation intensive. Furthermore, the noise model is highly customized and has to be tuned to a particular form-factor since noise that is actually induced in the PPG signal can differ significantly from motion noise measured by the motion sensor.

In contrast, embodiments that involve a synchronized averaging technique that can enhance PPG waves and cancel out random phase-varying motion noise. Additionally, embodiments use less computation and memory resources than some existing techniques without distorting or eliminating true PPG peaks. Furthermore, embodiments do not require separate noise sensors in hardware or a customized noise model that is required in some existing techniques.

According to embodiments, the R-waves in an ECG signal can be used as anchor points to enable accurate averaging of a PPG signal in the presence of motion noise. Unlike some conventional averaging techniques, which rely on detection of PPG peaks in order to perform the average of a PPG signal, embodiments use the ECG signal to determine which segments of the PPG signal to average. The ECG signal is typically less susceptible to motion noise, and it is usually possible to accurately detect the R-waves of an ECG signal in the presence of motion noise. This is at least partially because the R-waves are sharp, high amplitude peaks that are outside the frequency band of typical motion noise. Therefore, unlike the peaks in the PPG signal, the R-waves in an ECG signal are typically extractable using traditional signal processing techniques. Thus, in one embodiment, the PPG averaging logic 706 exploits the robustness of ECG R-wave detection to suppress motion noise in the PPG signal and detect the true PPG peaks. For example, the PPG averaging logic 706 uses the detected R-wave peaks as anchor points to define segments of the PPG signal to average. In one such embodiment, the PPG averaging logic 706 aligns a start time of a given PPG segment with a detected R-wave peak in the ECG signal. In this way, the PPG averaging logic 706 identifies segments of the PPG signal, or acquires sets of samples (e.g., one set of samples per R-wave peak), to average.

After identifying segments of the PPG signal for averaging based on the ECG signal, the PPG averaging logic 706 computes an average PPG wave, in accordance with embodiments. For example, in one embodiment, the PPG averaging logic 706 computes an average of corresponding samples from multiple segments to generate an averaged PPG wave. Unlike an averaged PPG wave obtained by traditional techniques in which the true PPG peaks can be shifted or entirely masked, computing an average using segments identified using the ECG signal as an anchor can enable extracting the true PPG peaks from the PPG signal in the presence of motion noise.

The blood pressure estimation logic 700 also includes PTT logic 708 to compute a PTT value. As mentioned above, PTT logic 708 can compute a PTT value based on the ECG and PPG signals. In accordance with one embodiment, the PTT logic 708 determines the PTT value based on the averaged PPG value that was computed using the R-waves of the ECG signal as an anchor. Thus, the PTT logic 708 can enable more accurate computation of PTT when a user is in motion. The blood pressure estimation logic 700 can also include blood pressure logic 710 to compute a blood pressure value based on the PTT value determined by the PTT logic 708. In other embodiments, one or more computations can be performed on an external device (e.g., the external computing device 407 of FIG. 4).

Figure 8:
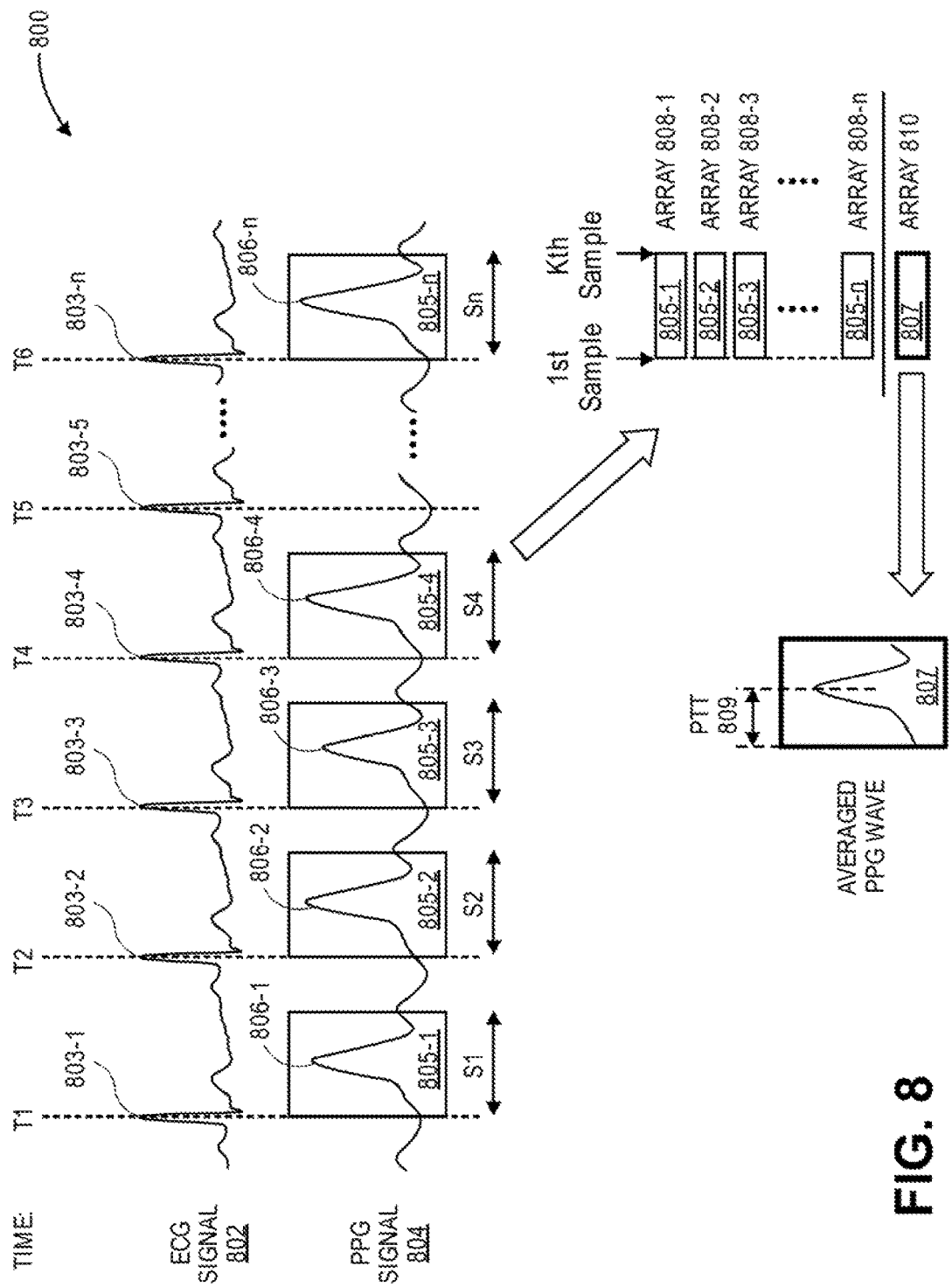
FIG. 8 illustrates a method of determining a blood pressure value, in accordance with an embodiment.

FIG. 8 illustrates a method 800 of computing an average PPG wave, in accordance with an embodiment. The method 800 involves averaging successive PPG waveforms synchronized to corresponding R-wave peaks in an ECG signal, in accordance with an embodiment. Unlike existing techniques that involve averaging based on a single signal, the method 800 involves computing an average PPG wave using both an ECG signal and a PPG signal. By anchoring the PPG signal to the ECG signal, embodiments enable motion noise reduction in a PPG signal.

The method 800 involves receiving an ECG signal 802 from an ECG sensor, such as the ECG sensors described above with respect to FIGS. 4 and 5. As mentioned above, the ECG signal 802 has sharp R-wave peaks 803-1-803-n. Although the ECG signal can also experience motion noise, traditional signal processing techniques can typically enable extraction of the R-wave peaks in the ECG signal despite the presence of motion noise. Furthermore, the motion noise (in the PPG signal 804) tends to have peaks that are not in synchrony with the ECG signal's R-wave peaks. The phase of the motion-noise peaks in the PPG signal continuously changes with respect to the R-wave peaks in the ECG signal, and tends to average out to zero over time. In contrast to the motion-noise peaks in the PPG signal, the PPG signal peaks 806-1-806-n are periodic and tightly synchronized in phase (e.g., phase-locked) with respect to the ECG R-wave peaks 803-1-803-n. Thus, the method 800 exploits the randomness property of motion noise in the PPG signal as well as the periodic and phase-locked property of the PPG peaks with respect to the ECG R-wave peaks to suppress motion noise. In one embodiment, the method involves selectively averaging successive segments of PPG waves that are aligned to R-wave peaks to derive a synthetic averaged PPG wave. Due to such synchronized averaging, the non-periodic motion noise tends to get canceled out in the averaged PPG wave, in accordance with embodiments. Furthermore, according to embodiments, the phase-locked PPG peaks tend to self-alight and get enhanced, which enables more accurate PPT estimation. Accordingly, embodiments enable suppression of noise in a PPG signal that would otherwise not be possible with traditional methods.

Referring again to FIG. 8, the method 800 involves detecting R-wave peaks 803-1-803-n in the ECG signal 802. In the illustrated embodiment, the ECG R-wave peaks 803-1-803-n are shown at times T1, T2, T3, T4, T5, and T6. In some embodiments, prior to detecting peaks, the method can involve signal processing techniques such as digital bandpass filtering to filter out motion noise from the ECG signal 802. After detection of the R-wave peaks 803-1-803-n, the method involves identifying multiple segments of the PPG signal based on detection of the R-wave peaks of the ECG signal, wherein a given segment includes multiple PPG samples and is aligned with a corresponding R-wave peak. For example, in one embodiment, the method involves identifying the segments S1-Sn of the PPG signal 804 with k samples each, starting from the occurrence of a corresponding ECG R-wave peak. The segments S1-Sn can also be referred to as sections of the PPG signal or sets of PPG samples. In one embodiment, the value k (the number of samples per window) is a positive integer, and is less than the number of samples between two successive ECG R-wave peaks. Dividing the PPG signal 804 into multiple PPG segments based on the detection of the R-waves 803-1-803-n results in multiple segments or sets 805-1-805-n of PPG samples. In the each illustrated embodiment, each segment 805-1-805-n includes k samples. Note that in the embodiment illustrated in FIG. 8, the segments 805-1-805-n do not comprise all PPG samples of the PPG signal. Instead, in one embodiment, a given segment of the PPG signal starts at the detection of an R-wave peak, and continues for k PPG samples. Thus, the segments 805-1-805-n include a subset of PPG samples, in accordance with embodiments. The method continues for n segments (or windows) to acquire n segments 805-1-805-n, each with k PPG samples. In one embodiment, the value n is a positive integer and is in a range to enable noise suppression without sacrificing responsiveness to changes in PTT. For example, in one embodiment, the number of segments of PPG samples is between 10-30. However, other embodiments can average less than 10 segments or more than 30. Larger values of n can offer better noise suppression but can be less responsive to fine-grained changes in PTT.

In one embodiment, the method involves saving the k samples acquired for each segment to an array. The array can be a software construct or hardware. In accordance with an embodiment, the method stores k samples for each of n segments to n one-dimensional arrays. Once the segments 805-1-805-n of PPG samples are stored into n arrays, the method 800 involves adding and averaging the corresponding elements in each of the n arrays. For example, element 1 in each of the arrays 808-1-808-n is added and averaged, element 2 in each of the arrays 808-1-808-n is added and averaged, and so on for each element in the arrays. Averaging the corresponding elements can involve computing a mean average of the corresponding elements, or other averaging technique. In one embodiment, the averaged elements are saved in another array 810 that also contains k elements. Each element of the array 810 contains the average of the corresponding element in the n arrays 808-1-808-n, in accordance with an embodiment. For example, the first element of the array 810 is to store an average of the first elements from the arrays 808-1-808-n. The array 810 thus stores the averaged PPG waveform 807. In one embodiment, because PPG peaks are phase-locked to R-wave peaks, the PPG peaks self-align in the averaging process, and thus become enhanced. Furthermore, because the motion noise is random and changes phase randomly with respect to the R-wave peaks, the noise tends to get suppressed in the averaging process.

The method 800 can then determine the PTT 809 based on the averaged PPG wave 807. In one embodiment, the location of the PPG peak in the array 810 corresponds to the PTT because the first element of the array was anchored to the R-wave peak. Accordingly, an ECG-synchronized PPG averaging method such as the method 800 of FIG. 8 can enable extraction of PTT reliably when a user is in motion. The blood pressure can then be estimated based on PTT.

Figure 9A:
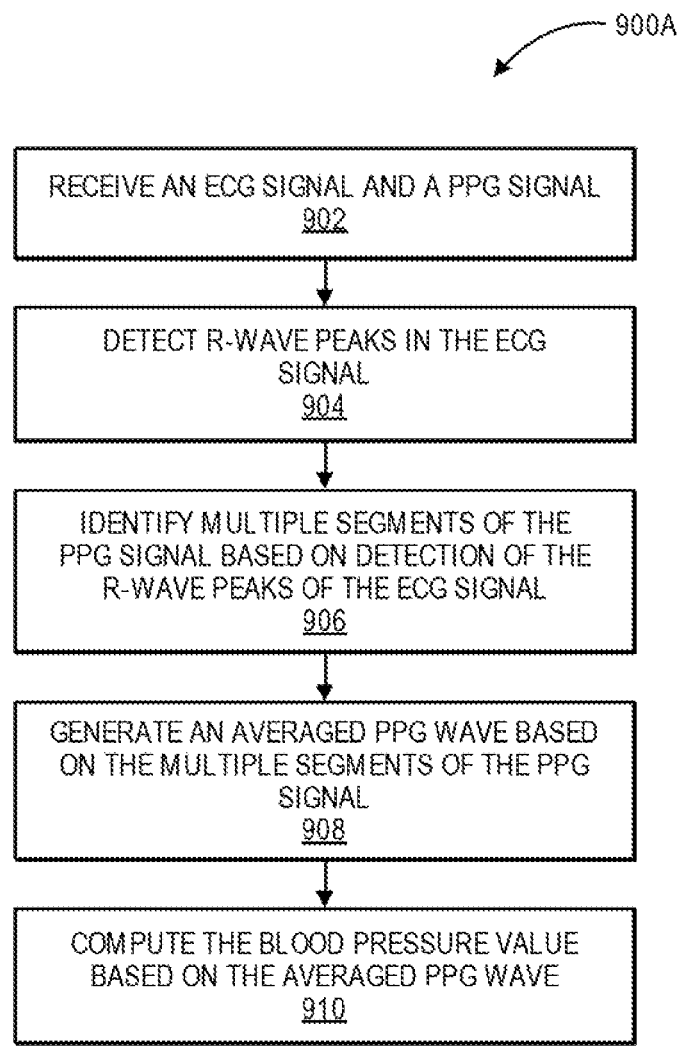
FIGS. 9A and 9B are flow charts of methods of determining a blood pressure value, in accordance with an embodiment.

FIG. 9A is a flow chart of a method 900A of determining a blood pressure value, in accordance with an embodiment. The method 900A can be the same or similar to the method 800 described above with respect to FIG. 8. The method 900A can be performed by hardware, software, or a combination of hardware and software. For example, the method 900A can be performed by the blood pressure measurement device of FIG. 405.

The method 900A beings with receiving an ECG signal and a PPG signal, at operation 902. For example, I/O circuitry (such as the I/O circuitry 417 of FIG. 4) receives an ECG signal from an ECG sensor and a PPG signal from a PPG sensor. I/O circuitry can receive the ECG and PPG signals from sensors, such as a PPG sensor and ECG sensor as illustrated in FIG. 4. Blood pressure estimation logic then performs a number of operations to estimate a user's blood pressure based on the received PPG and ECG signals. For example, the blood pressure estimation logic also detects R-wave peaks in the ECG signal (e.g., with R-wave detection logic 702 of FIG. 7), at operation 904. In some embodiments, in order to detect the R-wave peaks in the ECG signal in the presence of motion noise, the blood pressure estimation logic first performs digital signal processing techniques on the ECG signal to remove or suppress motion noise. For example, the blood pressure estimation logic can perform digital band pass filtering to generate a clean ECG signal in which the R-waves are detectable.

The blood pressure estimation logic can then identify multiple segments of the PPG signal based on detection of the R-wave peaks (e.g., with the PPG averaging logic 706 of FIG. 7), at operation 906. For example, as describe above with respect to FIG. 8, the blood pressure estimation logic can identify and/or store multiple segments or sets of PPG samples (e.g., the segments 805-1-805-n) based on detection of corresponding R-wave peaks. In one embodiment, the blood pressure estimation logic can identify a first sample for each segment in response to detection of a corresponding R-wave peak.

After identifying the PPG segments, the blood pressure estimation logic can then generate an average PPG wave, at operation 908. For example, the blood pressure estimation logic can compute an average of corresponding samples from the multiple segments to generate an averaged PPG wave. The average PPG wave can be computed in accordance with the method 800 of FIG. 8, described above.

Based on the average PPG wave, the blood pressure estimation logic can then compute the blood pressure value based on the averaged PPG wave, at operation 910.

Figure 9B:
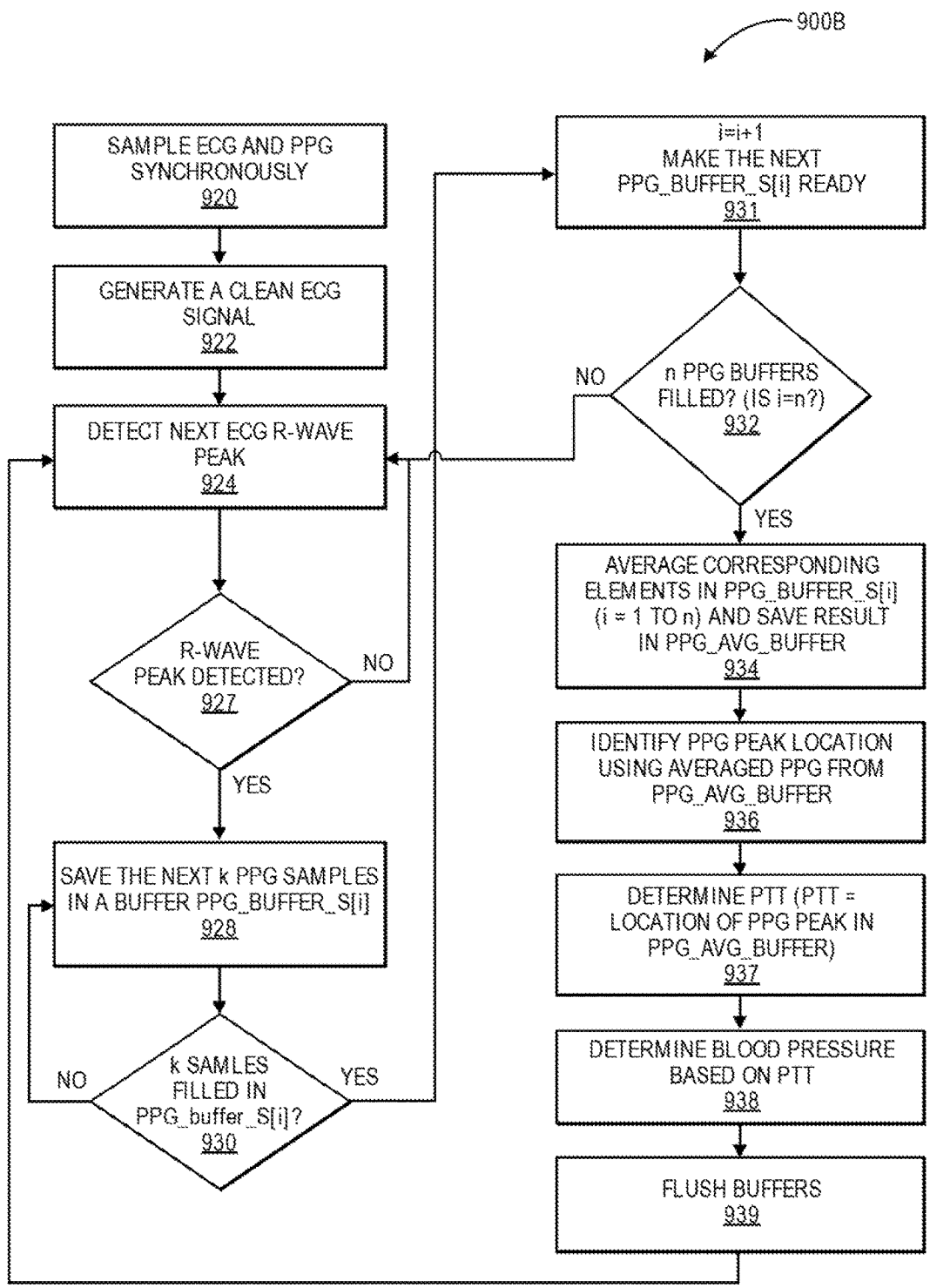

FIG. 9B is a flow chart of a method 900B of determining blood pressure, in accordance with an embodiment. The method 900B is an example of the method 900A, in accordance with an embodiment. The method 900B can be performed by hardware, software, or a combination of hardware and software. For example, the method 900B can be performed by the blood pressure measurement device of FIG. 405.

The method 900B begins with sampling ECG and PPG synchronously, at operation 920. For example, in one embodiment, blood pressure estimation logic (such as the blood pressure estimation logic 415 of FIG. 4) samples the ECG and PPG signals at the same sampling rate. The method then involves generating a clean ECG signal, at operation 922. For example, the blood pressure estimation logic (such as the R-wave detection logic 702 of FIG. 7) processes the ECG signal through a band pass filter to enable extraction of the R-waves and detection of the R-wave peaks. R-wave detection logic can then detect the next R-wave peak in the ECG signal, at operation 924. Once an R-wave peak is detected, 927 YES branch, the blood pressure estimation logic (e.g., the PPG averaging logic 706) saves the next k PPG samples in a buffer. In accordance with an embodiment, the k PPG samples defines a single segment of the PPG signal. If the R-wave peak is not detected, 927 NO branch, the R-wave detection logic continues to attempt to detect the next ECG R-wave peak, at operation 924. The blood pressure estimation logic repeats the process of detecting the next R-wave peak and storing the next k PPG samples in a buffer until n buffers are filled. The numbers k and n can be the same or similar to the numbers k and n described above with respect to FIG. 8.

In the illustrated embodiment, the PPG averaging logic saves the next k PPG samples in a buffer (e.g., PPG_BUFFER_S[i]), at operation 928. If the PPG averaging logic has not saved all k samples in the buffer, 930 NO branch, the PPG averaging logic continues to save samples in the buffer until k samples have been saved, at operation 928. Once the PPG averaging logic has saved k samples in the buffer, 930 YES branch, the PPG averaging logic moves to the next buffer (e.g., i=i+1 to make the next PPG_BUFFER_S[i] ready) for filling in the next k samples, at operation 931. For example, after PPG_BUFFER_S[1] is filled with k PPG samples, the PPG averaging logic allocates memory for the next buffer, PPG_BUFFER_S[2]. The PPG averaging logic repeats the operations of saving k samples based on detection of an R-wave peak n times. For example, as illustrated in FIG. 9B, if n PPG buffers are not filled (e.g., if i is not equal to n), the R-wave detection logic continues to attempt to detect the next R-wave peaks at operation 924 and the PPG averaging logic continues to save the next k PPG samples in a buffer in response to detection of the R-wave peak, at operation 928.

Once n PPG buffers are filled, 932 YES branch, the PPG averaging logic averages corresponding elements in PPG_BUFFER_S[i] (e.g., i=1 to n) and saves the result in another buffer (e.g., PPG_AVG_BUFFER), at operation 934. For example, PPG averaging logic averages corresponding k elements in all the n PPG segment buffers and creates a new PPG_AVG_BUFFER (e.g., allocates memory for the buffer) that holds the synchronously averaged PPG waveform. The location of a PPG peak can then be determined using the averaged PPG waveform, at operation 936. Unlike conventional PPG averaging techniques, the synchronously averaged PPG waveform results in an enhanced PPG peak, in accordance with embodiments. In accordance with embodiments, PPG average waveform is phase-locked to the R-wave peaks, and therefore enables suppression of motion noise, which is random in phase with respect to the R-wave peaks. Accordingly, the method 900B enables determination of an average PPG wave that is significantly more accurate in the presence of motion noise than conventional techniques.

After generating the average PPG waveform, logic (e.g., PTT logic 708 of FIG. 7) can determine PTT based on the average PPG waveform, at operation 937. In the embodiment illustrated in FIG. 9B, the PTT is the horizontal location of the PPG peak of the average PPG waveform (e.g., the averaged PPG stored in PPG_AVG_BUFFER) times sampling time. After computing PTT, logic (e.g., blood pressure logic 710 of FIG. 7) can estimate a blood pressure value based on the PTT, at operation 938. The blood pressure estimation logic can then flush all the buffers, at operation 939, and the R-wave peak detection process can begin again. Thus, using ECG R-wave peaks as anchor points to precisely select PPG waveform segments and averaging those segments can enable efficient motion noise suppression in the PPG signal. Efficient motion noise suppression in the PPG signal can then enable accurate blood pressure determination without a blood pressure cuff in the presence of motion noise, in accordance with embodiments.

Figure 10:
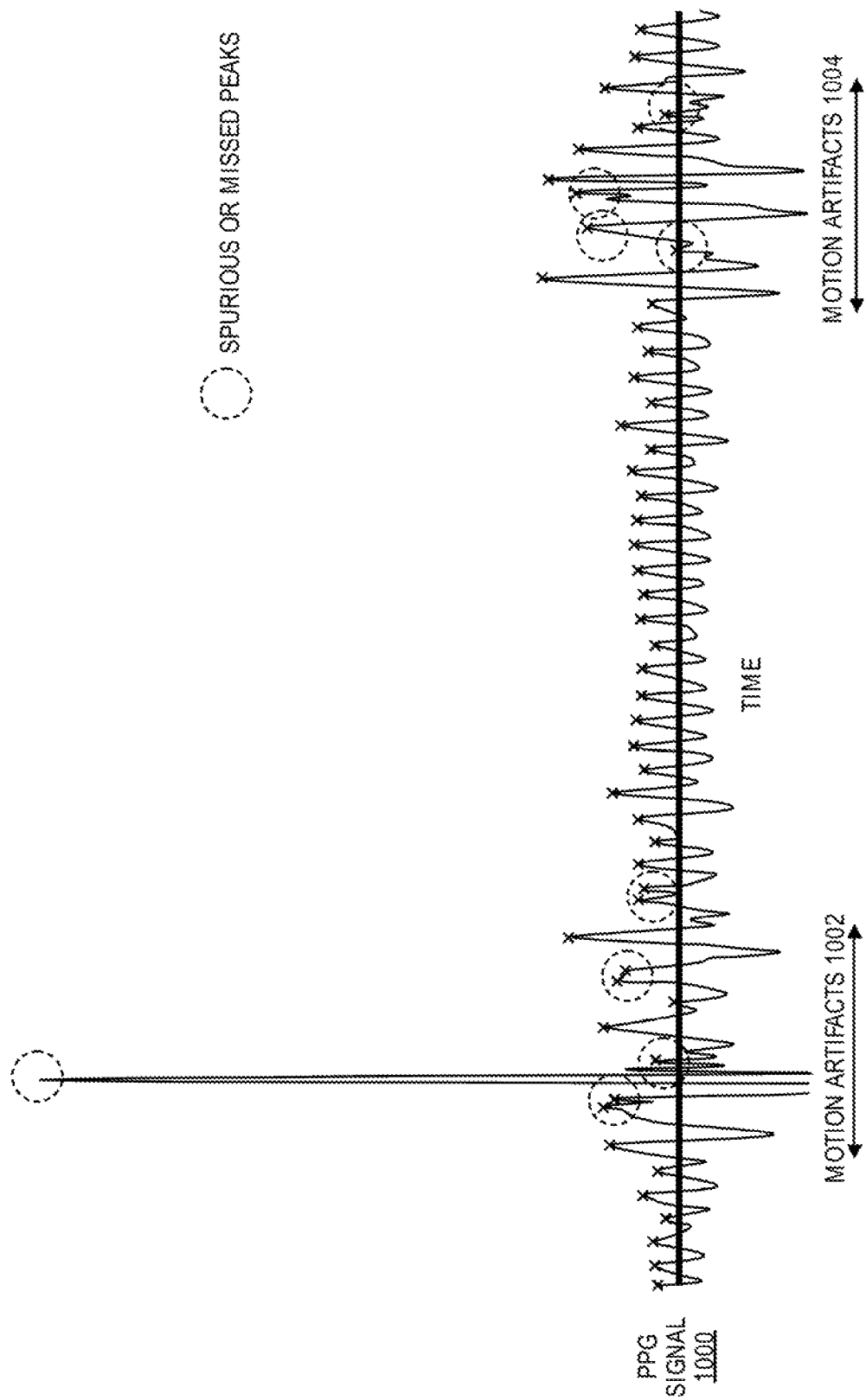
FIG. 10 is a graph showing a PPG signal with motion artifacts, in accordance with an embodiment.

FIG. 10 is a graph showing a PPG waveform with motion artifacts, in accordance with an embodiment. PPG peaks detected by conventional techniques are shown with an 'x' on the detected peaks. For reasons described above, conventional signal processing techniques are typically ineffective at removing motion noise from a PPG signal, which in some cases results in the detection of false or spurious PPG peaks as PPG peaks. In some cases, the noise can completely mask the true PPG peaks, which are then missed by conventional techniques for detecting PPG peaks. In the example illustrated in FIG. 10, a PPG signal 1000 includes two segments with motion artifacts 1002 and 1004. The motion artifacts 1002 and 1004 are an example of motion artifacts or noise caused by walking or other movement of the user. The dotted-line circles indicate spurious or missed peaks resulting from the motion noise when conventional techniques are employed.

Figure 11A:
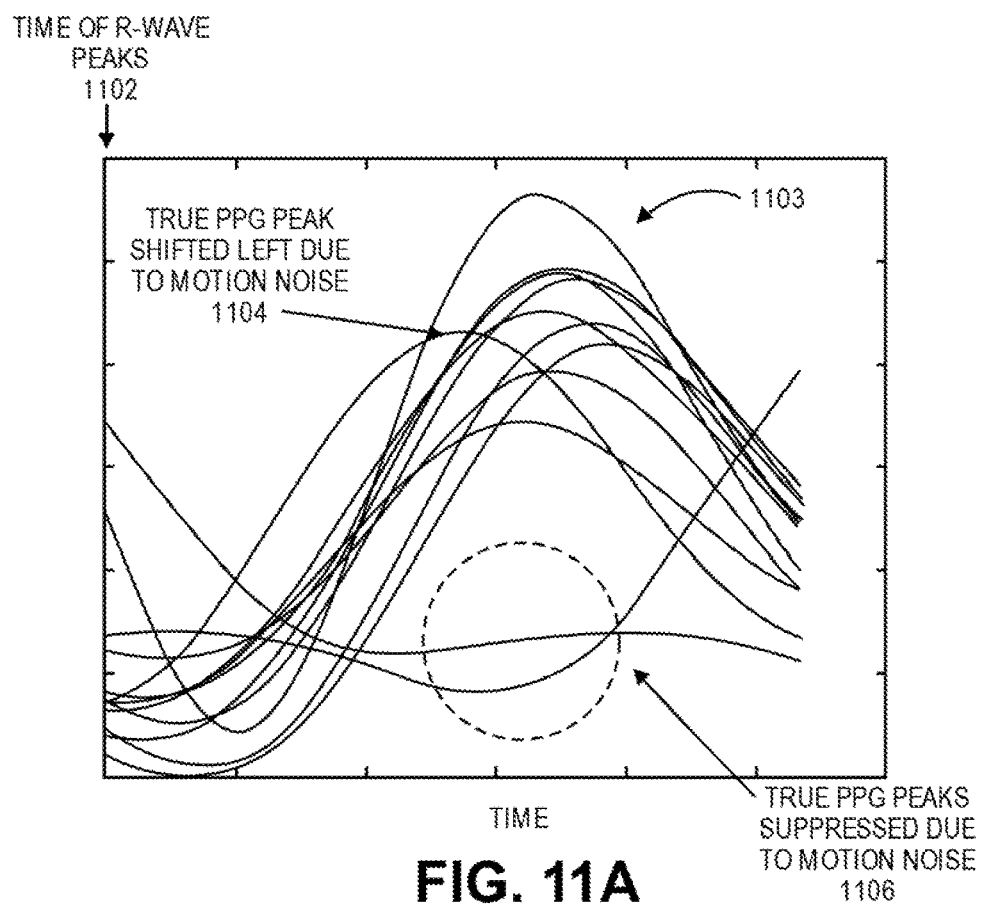
FIGS. 11A and 11B illustrate an averaged PPG waveform based on the PPG signal of FIG. 10, in accordance with embodiments.
Figure 11B:
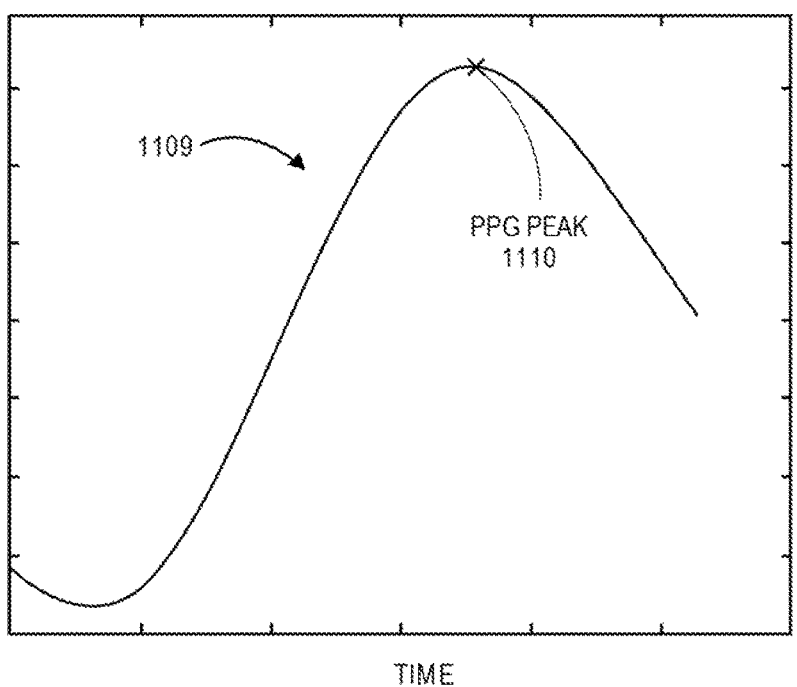

In contrast, FIGS. 11A and 11B illustrate an average PPG waveform in accordance with embodiments described herein, which enables detection of the true PPG peak in the presence of motion noise. The graph in FIG. 11A illustrates the individual PPG segments 1103 (e.g., such as the segments 805-1-805-n of FIG. 8) with motion noise superimposed onto a single graph. Each segment is from a window that starts at a time of a corresponding R-wave peak, as indicated by the arrow 1102. As can be seen in the graph, some PPG peaks are shifted due to motion noise (such as peak 1104, which is shifted left). Other peaks are suppressed or masked due to motion noise (such as the suppressed peak 1106). However, techniques of averaging as described herein that use both the PPG and ECG signals can enable suppression of motion noise and extraction of the true PPG peak. For example, the graph of FIG. 11B illustrates the averaged PPG waveform 1109 in accordance with embodiments described herein. The waveform 1109 is obtained by adding and averaging the corresponding elements of the segments 1103 of FIG. 11A. Despite the presence of shifted and masked peaks in some of the segments 1103, the method of determining the average PPG wave based on the R-wave peaks of the ECG signal results in the extraction of a noise-free averaged PPG wave 1109 in which the PPG peak 1110 is not significantly shifted, and can even be enhanced. As can be seen in FIG. 11B, the methods of computing an averaged PPG waveform described herein can suppress motion noise and enable detection of true PPG peaks in the presence of motion noise.

Figure 12:
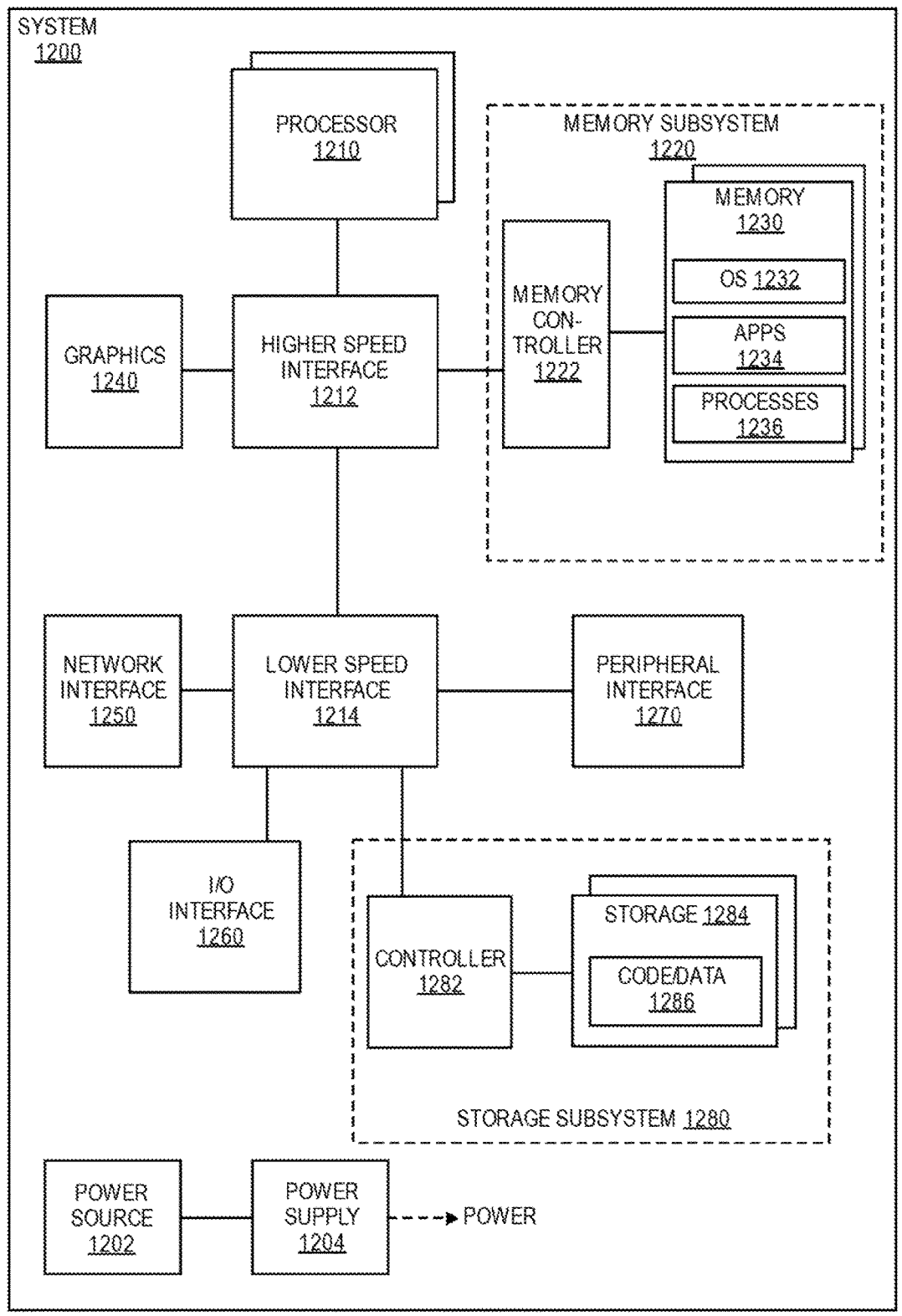
FIG. 12 is a block diagram of a computing system in which a method of determining blood pressure can be implemented, in accordance with an embodiment.

FIG. 12 is a block diagram of a computing system in which a method of determining blood pressure can be implemented, in accordance with an embodiment. As discussed above, one or more of the operations in the methods described herein can be performed by a blood pressure measuring device (e.g., the wearable blood pressure measurement device 405 of FIG. 4), or by an external computing device, such as the system 1200 of FIG. 12.

System 1200 represents a computing device in accordance with any embodiment described herein, and can be a laptop computer, a desktop computer, a server, a gaming or entertainment control system, a scanner, copier, printer, routing or switching device, embedded computing device, or other electronic device.

System 1200 includes processor 1210, which provides processing, operation management, and execution of instructions for system 1200. Processor 1210 can include any type of microprocessor, central processing unit (CPU), graphics processing unit (GPU), processing core, or other processing hardware to provide processing for system 1200, or a combination of processors. Processor 1210 controls the overall operation of system 1200, and can be or include, one or more programmable general-purpose or special-purpose microprocessors, digital signal processors (DSPs), programmable controllers, application specific integrated circuits (ASICs), programmable logic devices (PLDs), or the like, or a combination of such devices.

In one embodiment, system 1200 includes interface 1212 coupled to processor 1210, which can represent a higher speed interface or a high throughput interface for system components that needs higher bandwidth connections, such as memory subsystem 1220 or graphics interface components 1240. Interface 1212 can represent a "north bridge" circuit, which can be a standalone component or integrated onto a processor die. Graphics interface 1240 interfaces to graphics components for providing a visual display to a user of system 1200. In one embodiment, graphics interface 1240 generates a display based on data stored in memory 1230 or based on operations executed by processor 1210 or both.

Memory subsystem 1220 represents the main memory of system 1200, and provides storage for code to be executed by processor 1210, or data values to be used in executing a routine. Memory subsystem 1220 can include one or more memory devices 1230 such as read-only memory (ROM), flash memory, one or more varieties of random access memory (RAM), or other memory devices, or a combination of such devices.

Memory 1230 stores and hosts, among other things, operating system (OS) 1232 to provide a software platform for execution of instructions in system 1200. Additionally, applications 1234 can execute on the software platform of OS 1232 from memory 1230. Applications 1234 represent programs that have their own operational logic to perform execution of one or more functions. Processes 1236 represent agents or routines that provide auxiliary functions to OS 1232 or one or more applications 1234 or a combination. OS 1232, applications 1234, and processes 1236 provide logic to provide functions for system 1200. In one embodiment, memory subsystem 1220 includes memory controller 1222, which is a memory controller to generate and issue commands to memory 1230. It will be understood that memory controller 1222 could be a physical part of processor 1210 or a physical part of interface 1212. For example, memory controller 1222 can be an integrated memory controller, integrated onto a circuit with processor 1210.

While not specifically illustrated, it will be understood that system 1200 can include one or more buses or bus systems between devices, such as a memory bus, a graphics bus, interface buses, or others. Buses or other signal lines can communicatively or electrically couple components together, or both communicatively and electrically couple the components. Buses can include physical communication lines, point-to-point connections, bridges, adapters, controllers, or other circuitry or a combination. Buses can include, for example, one or more of a system bus, a Peripheral Component Interconnect (PCI) bus, a HyperTransport or industry standard architecture (ISA) bus, a small computer system interface (SCSI) bus, a universal serial bus (USB), or an Institute of Electrical and Electronics Engineers (IEEE) standard 1394 bus (commonly referred to as "Firewire").

In one embodiment, system 1200 includes interface 1214, which can be coupled to interface 1212. Interface 1214 can be a lower speed interface than interface 1212. In one embodiment, interface 1214 can be a "south bridge" circuit, which can include standalone components and integrated circuitry. In one embodiment, multiple user interface components or peripheral components, or both, couple to interface 1214. Network interface 1250 provides system 1200 the ability to communicate with remote devices (e.g., servers or other computing devices) over one or more networks. Network interface 1250 can include an Ethernet adapter, wireless interconnection components, USB (universal serial bus), or other wired or wireless standards-based or proprietary interfaces. Network interface 1250 can exchange data with a remote device, which can include sending data stored in memory or receiving data to be stored in memory.

In one embodiment, system 1200 includes one or more input/output (I/O) interface(s) 1260. I/O interface 1260 can include one or more interface components through which a user interacts with system 1200 (e.g., audio, alphanumeric, tactile/touch, or other interfacing). Peripheral interface 1270 can include any hardware interface not specifically mentioned above. Peripherals refer generally to devices that connect dependently to system 1200. A dependent connection is one where system 1200 provides the software platform or hardware platform or both on which operation executes, and with which a user interacts.

In one embodiment, system 1200 includes storage subsystem 1280 to store data in a nonvolatile manner. In one embodiment, in certain system implementations, at least certain components of storage 1280 can overlap with components of memory subsystem 1220. Storage subsystem 1280 includes storage device(s) 1284, which can be or include any conventional medium for storing large amounts of data in a nonvolatile manner, such as one or more magnetic, solid state, or optical based disks, or a combination. Storage 1284 holds code or instructions and data 1286 in a persistent state (i.e., the value is retained despite interruption of power to system 1200). Storage 1284 can be generically considered to be a "memory," although memory 1230 is typically the executing or operating memory to provide instructions to processor 1210. Whereas storage 1284 is nonvolatile, memory 1230 can include volatile memory (i.e., the value or state of the data is indeterminate if power is interrupted to system 1200). In one embodiment, storage subsystem 1280 includes controller 1282 to interface with storage 1284. In one embodiment controller 1282 is a physical part of interface 1214 or processor 1210, or can include circuits or logic in both processor 1210 and interface 1214.

Power source 1202 provides power to the components of system 1200. More specifically, power source 1202 typically interfaces to one or multiple power supplies 1204 in system 1200 to provide power to the components of system 1200. In one embodiment, power supply 1204 includes an AC to DC (alternating current to direct current) adapter to plug into a wall outlet. Such AC power can be renewable energy (e.g., solar power) power source 1202. In one embodiment, power source 1202 includes a DC power source, such as an external AC to DC converter. In one embodiment, power source 1202 or power supply 1204 includes wireless charging hardware to charge via proximity to a charging field. In one embodiment, power source 1202 can include an internal battery or fuel cell source.

Figure 13:
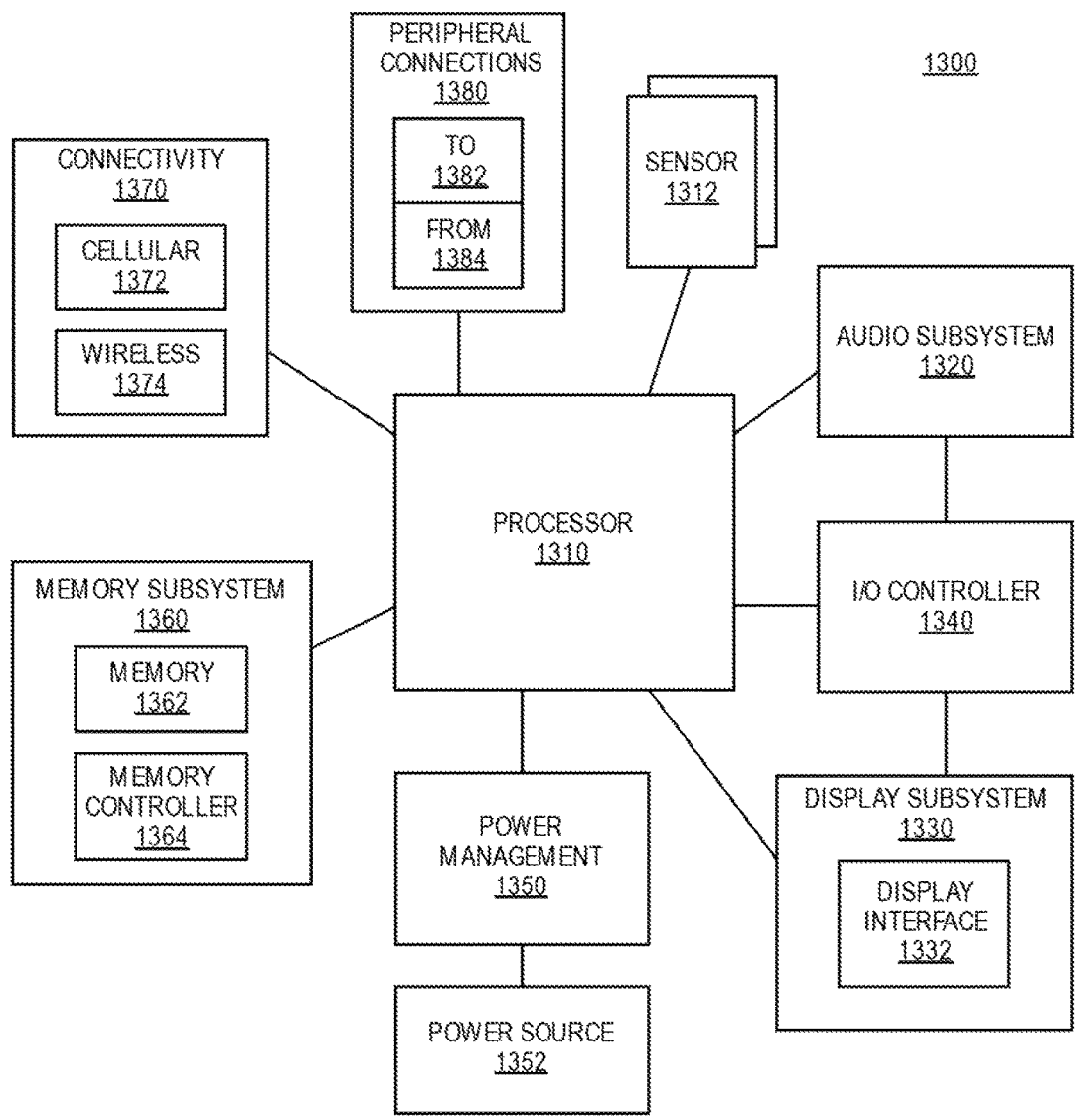
FIG. 13 is a block diagram of a mobile device in which a method of determining blood pressure can be implemented, in accordance with an embodiment.

FIG. 13 is a block diagram of a mobile device in which a method of determining blood pressure can be implemented, in accordance with an embodiment. Device 1200 represents a mobile computing device, such as a computing tablet, a mobile phone or smartphone, a wireless-enabled e-reader, wearable computing device, or other mobile device, or an embedded computing device. It will be understood that certain of the components are shown generally, and not all components of such a device are shown in device 1300.

Device 1300 includes processor 1310, which performs the primary processing operations of device 1300. Processor 1310 can include one or more physical devices, such as microprocessors, application processors, microcontrollers, programmable logic devices, or other processing means. The processing operations performed by processor 1310 include the execution of an operating platform or operating system on which applications and device functions are executed. The processing operations include operations related to I/O (input/output) with a human user or with other devices, operations related to power management, operations related to connecting device 1300 to another device, or a combination. The processing operations can also include operations related to audio I/O, display I/O, or other interfacing, or a combination. Processor 1310 can execute data stored in memory. Processor 1310 can write or edit data stored in memory.

In one embodiment, system 1300 includes one or more sensors 1312. Sensors 1312 represent embedded sensors or interfaces to external sensors, or a combination. Sensors 1312 enable system 1300 to monitor or detect one or more conditions of an environment or a device in which system 1300 is implemented. Sensors 1312 can include environmental sensors (such as temperature sensors, motion detectors, light detectors, cameras, chemical sensors (e.g., carbon monoxide, carbon dioxide, or other chemical sensors)), pressure sensors, accelerometers, gyroscopes, medical or physiology sensors (e.g., biosensors, heart rate monitors, glucose monitors, or other sensors to detect medical or physiological attributes), or other sensors, or a combination. Sensors 1312 can also include sensors for biometric systems such as fingerprint detectors, face detection or recognition systems, or other systems that detect or recognize user features. Sensors 1312 should be understood broadly, and not limiting on the many different types of sensors that could be implemented with system 1300. In one embodiment, one or more sensors 1312 couples to processor 1310 via a frontend circuit integrated with processor 1310. In one embodiment, one or more sensors 1312 couples to processor 1310 via another component of system 1300.

In one embodiment, device 1300 includes audio subsystem 1320, which represents hardware (e.g., audio hardware and audio circuits) and software (e.g., drivers, codecs) components associated with providing audio functions to the computing device. Audio functions can include speaker or headphone output, as well as microphone input. Devices for such functions can be integrated into device 1300, or connected to device 1300. In one embodiment, a user interacts with device 1300 by providing audio commands that are received and processed by processor 1310.

Display subsystem 1330 represents hardware (e.g., display devices) and software components (e.g., drivers) that provide a visual display for presentation to a user. In one embodiment, the display includes tactile components or touchscreen elements for a user to interact with the computing device. Display subsystem 1330 includes display interface 1332, which includes the particular screen or hardware device used to provide a display to a user. In one embodiment, display interface 1332 includes logic separate from processor 1310 (such as a graphics processor) to perform at least some processing related to the display. In one embodiment, display subsystem 1330 includes a touchscreen device that provides both output and input to a user. In one embodiment, display subsystem 1330 includes a high definition (HD) display that provides an output to a user. High definition can refer to a display having a pixel density of approximately 100 PPI (pixels per inch) or greater, and can include formats such as full HD (e.g., 1080p), retina displays, 4K (ultra high definition or UHD), or others. In one embodiment, display subsystem 1330 generates display information based on data stored in memory and operations executed by processor 1310.

I/O controller 1340 represents hardware devices and software components related to interaction with a user. I/O controller 1340 can operate to manage hardware that is part of audio subsystem 1320, or display subsystem 1330, or both. Additionally, I/O controller 1340 illustrates a connection point for additional devices that connect to device 1300 through which a user might interact with the system. For example, devices that can be attached to device 1300 might include microphone devices, speaker or stereo systems, video systems or other display device, keyboard or keypad devices, or other I/O devices for use with specific applications such as card readers or other devices.

As mentioned above, I/O controller 1340 can interact with audio subsystem 1320 or display subsystem 1330 or both. For example, input through a microphone or other audio device can provide input or commands for one or more applications or functions of device 1300. Additionally, audio output can be provided instead of or in addition to display output. In another example, if display subsystem includes a touchscreen, the display device also acts as an input device, which can be at least partially managed by I/O controller 1340. There can also be additional buttons or switches on device 1300 to provide I/O functions managed by I/O controller 1340.

In one embodiment, I/O controller 1340 manages devices such as sensors 1312, accelerometers, cameras, light sensors or other environmental sensors, gyroscopes, global positioning system (GPS), or other hardware that can be included in device 1300. The input can be part of direct user interaction, as well as providing environmental input to the system to influence its operations (such as filtering for noise, adjusting displays for brightness detection, applying a flash for a camera, or other features).

In one embodiment, device 1300 includes power management 1350 that manages battery power usage, charging of the battery, and features related to power saving operation. Power management 1350 manages power from power source 1352, which provides power to the components of system 1300. In one embodiment, power source 1352 includes an AC to DC (alternating current to direct current) adapter to plug into a wall outlet. Such AC power can be renewable energy (e.g., solar power, motion based power). In one embodiment, power source 1352 includes only DC power, which can be provided by a DC power source, such as an external AC to DC converter. In one embodiment, power source 1352 includes wireless charging hardware to charge via proximity to a charging field. In one embodiment, power source 1352 can include an internal battery or fuel cell source.

Memory subsystem 1360 includes memory device(s) 1362 for storing information in device 1300. Memory subsystem 1360 can include nonvolatile (state does not change if power to the memory device is interrupted) or volatile (state is indeterminate if power to the memory device is interrupted) memory devices, or a combination. Memory 1360 can store application data, user data, music, photos, documents, or other data, as well as system data (whether long-term or temporary) related to the execution of the applications and functions of system 1300. In one embodiment, memory subsystem 1360 includes memory controller 1364 (which could also be considered part of the control of system 1300, and could potentially be considered part of processor 1310). Memory controller 1364 includes a scheduler to generate and issue commands to memory device 1362. The device 1300 also include a storage subsystem 1306. The storage subsystem 1306 includes one or more storage devices 1301 and a controller 1305 for controlling access to the storage devices 1301.

Connectivity 1370 includes hardware devices (e.g., wireless or wired connectors and communication hardware, or a combination of wired and wireless hardware) and software components (e.g., drivers, protocol stacks) to enable device 1300 to communicate with external devices. The external device could be separate devices, such as other computing devices, wireless access points or base stations, as well as peripherals such as headsets, printers, or other devices. In one embodiment, system 130 exchanges data with an external device for storage in memory or for display on a display device. The exchanged data can include data to be stored in memory, or data already stored in memory, to read, write, or edit data.

Connectivity 1370 can include multiple different types of connectivity. To generalize, device 1300 is illustrated with cellular connectivity 1372 and wireless connectivity 1374. Cellular connectivity 1372 refers generally to cellular network connectivity provided by wireless carriers, such as provided via GSM (global system for mobile communications) or variations or derivatives, CDMA (code division multiple access) or variations or derivatives, TDM (time division multiplexing) or variations or derivatives, LTE (long term evolution also referred to as "4G"), or other cellular service standards. Wireless connectivity 1374 refers to wireless connectivity that is not cellular, and can include personal area networks (such as Bluetooth®), local area networks (such as WiFi), or wide area networks (such as WiMax), or other wireless communication, or a combination. Wireless communication refers to transfer of data through the use of modulated electromagnetic radiation through a non-solid medium. Wired communication occurs through a solid communication medium.

Peripheral connections 1380 include hardware interfaces and connectors, as well as software components (e.g., drivers, protocol stacks) to make peripheral connections. It will be understood that device 1300 could both be a peripheral device ("to" 1382) to other computing devices, as well as have peripheral devices ("from" 1384) connected to it. Device 1300 commonly has a "docking" connector to connect to other computing devices for purposes such as managing (e.g., downloading, uploading, changing, synchronizing) content on device 1300. Additionally, a docking connector can allow device 1300 to connect to certain peripherals that allow device 1300 to control content output, for example, to audiovisual or other systems.

In addition to a proprietary docking connector or other proprietary connection hardware, device 1300 can make peripheral connections 1380 via common or standards-based connectors. Common types can include a Universal Serial Bus (USB) connector (which can include any of a number of different hardware interfaces), DisplayPort including MiniDisplayPort (MDP), High Definition Multimedia Interface (HDMI), Firewire, or other type.

Some embodiments of the disclosure follow. In one embodiment, an apparatus for determining a blood pressure value includes I/O circuitry to receive an electrocardiographic (ECG) signal and a photoplethysmographic (PPG) signal, and blood pressure estimation logic to: detect R-wave peaks of the ECG signal, identify multiple segments of the PPG signal based on detection of the R-wave peaks of the ECG signal, wherein a given segment of the PPG signal comprises multiple PPG samples and is aligned with a corresponding R-wave peak, and generate an averaged PPG wave based on the multiple segments of the PPG signal, wherein a given element of the averaged PPG wave comprises an average of corresponding elements from the multiple segments of the PPG signal. The blood pressure estimation logic is also to compute the blood pressure value based on the averaged PPG wave, in accordance with an embodiment.

In one embodiment, each segment includes k samples, and the blood pressure estimation logic is to: for each i=1 to k, add the ith samples of the multiple segments together and compute an average, wherein the ith element of the averaged PPG wave includes the computed average of the ith samples of the multiple segments. In one such embodiment, k is less than or equal to a number of samples between successive R-wave peaks of the ECG signal. In one embodiment, the apparatus further includes an ECG sensor to detect the ECG signal, wherein the ECG sensor is coupled with the I/O circuitry and includes electrodes on a wearable patch. In one embodiment, the sensor further includes a PPG sensor to detect the PPG signal, wherein the PPG sensor is coupled with the I/O circuitry and includes a light emitting diode (LED) and a photodiode on a wearable patch.

In one embodiment, the apparatus further includes a storage array to store the multiple segments of the PPG signal and the averaged PPG wave. In one embodiment, the blood pressure estimation logic is to: detect a PPG peak in the averaged PPG wave, determine pulse transmit time (PTT) based on a time difference between an ECG R-wave peak and the PPG peak of the averaged PPG wave, and compute an estimate of the blood pressure value based on the PTT. In one embodiment, the blood pressure estimation logic is to: for a given segment of the PPG signal, identify a first sample of the given segment in response to detection of the corresponding R-wave peak in the ECG signal. In one embodiment, the blood pressure estimation logic is to: for each segment of the PPG signal, identify a first sample of the segment in response to detection of the corresponding R-wave peak in the ECG signal, detect a PPG peak in the averaged PPG wave, determine pulse transmit time (PTT) based on a location of the PPG peak of the averaged PPG wave, compute an estimate of the blood pressure value based on the PTT.

In one embodiment, the PPG signal includes motion artifacts in a same frequency band as PPG peaks of the PPG signal. In one embodiment, the I/O circuitry is to further transmit the blood pressure value to a remote computing device.

In one embodiment, a method of determining a blood pressure value involves receiving an electrocardiographic (ECG) signal and a photoplethysmographic (PPG) signal, detecting R-wave peaks in the ECG signal, identifying multiple segments of the PPG signal based on detection of the R-wave peaks of the ECG signal, wherein a given segment of the PPG signal comprises multiple PPG samples and is aligned with a corresponding R-wave peak, generating an averaged PPG wave based on the multiple segments of the PPG signal, wherein a given element of the averaged PPG wave comprises an average of corresponding elements from the multiple segments of the PPG signal, and computing the blood pressure value based on the averaged PPG wave. In one embodiment, each segment comprises k samples, and generating the averaged PPG wave involves: for each i=1 to k, adding the ith samples of the multiple segments together and computing an average, wherein the ith element of the averaged PPG wave comprises the computed average of the ith samples of the multiple segments.

In one embodiment, identifying the multiple segments of the PPG signal involves for a given segment of the PPG signal, identifying a first sample of the given segment in response to detection of the corresponding R-wave peak in the ECG signal. In one embodiment, the method further involves detecting the ECG signal with an ECG sensor including electrodes on a wearable patch. In one embodiment, the method further involves detecting the PPG signal with a PPG sensor on a wearable patch, the PPG sensor comprising a light emitting diode (LED) and a photodiode. In one embodiment, the method further involves detecting the ECG signal and the PPG signal with sensors on a wearable patch when a user of the wearable patch is in motion.

In one embodiment, an article of manufacture comprising a computer readable storage medium having content stored thereon which when accessed causes the performance of operations to execute a method including: receiving an electrocardiographic (ECG) signal and a photoplethysmographic (PPG) signal, detecting R-wave peaks in the ECG signal, identifying multiple segments of the PPG signal based on detection of the R-wave peaks of the ECG signal, wherein a given segment of the PPG signal comprises multiple PPG samples and is aligned with a corresponding R-wave peak, generating an averaged PPG wave based on the multiple segments of the PPG signal, wherein a given element of the averaged PPG wave comprises an average of corresponding elements from the multiple segments of the PPG signal, and computing a blood pressure value based on the averaged PPG wave.

In one embodiment, an apparatus for determining a blood pressure value includes means to receive an electrocardiographic (ECG) signal and a photoplethysmographic (PPG) signal, means to detect R-wave peaks of the ECG signal, identify multiple segments of the PPG signal based on detection of the R-wave peaks of the ECG signal, wherein a given segment of the PPG signal comprises multiple PPG samples and is aligned with a corresponding R-wave peak, generate an averaged PPG wave based on the multiple segments of the PPG signal, wherein a given element of the averaged PPG wave comprises an average of corresponding elements from the multiple segments of the PPG signal, and compute the blood pressure value based on the averaged PPG wave. In one embodiment, each segment comprises k samples, wherein the means to generate the averaged PPG wave comprise means to: for each i=1 to k, add the ith samples of the multiple segments together and compute an average, wherein the ith element of the averaged PPG wave includes the computed average of the ith samples of the multiple segments. In one embodiment, the apparatus further include means to detect the ECG signal. In one embodiment, the apparatus further includes means to detect the PPG signal. In one embodiment, the apparatus further includes a storage array to store the multiple segments of the PPG signal and the averaged PPG wave. In one embodiment, the apparatus further includes means to detect a PPG peak in the averaged PPG wave and means to determine pulse transmit time (PTT) based on a time difference between an ECG R-wave peak and the PPG peak of the averaged PPG wave, wherein the means to compute the blood pressure value includes means to estimate the blood pressure value based on the PTT.

In one embodiment, the means to generate the averaged PPG wave includes means to: for a given segment of the PPG signal, identify a first sample of the given segment in response to detection of the corresponding R-wave peak in the ECG signal. In one embodiment, the means for generating the averaged PPG form includes means to: for each segment of the PPG signal, identify a first sample of the segment in response to detection of the corresponding R-wave peak in the ECG signal, detect a PPG peak in the averaged PPG wave, and determine pulse transmit time (PTT) based on a location of the PPG peak of the averaged PPG wave, wherein the means to compute the blood pressure value includes means to estimate the blood pressure value based on the PTT. In one embodiment, the apparatus further includes means to transmit the blood pressure value to a remote computing device.

Various components described herein can be a means for performing the operations or functions described. Each component described herein includes software, hardware, or a combination of these. The components can be implemented as software modules, hardware modules, special-purpose hardware (e.g., application specific hardware, application specific integrated circuits (ASICs), digital signal processors (DSPs), etc.), embedded controllers, hardwired circuitry, etc.

Besides what is described herein, various modifications can be made to the disclosed embodiments and implementations of the invention without departing from their scope. Therefore, the illustrations and examples herein should be construed in an illustrative, and not a restrictive sense. The scope of the invention should be measured solely by reference to the claims that follow.

What is claimed is:

1. An apparatus for determining a blood pressure value, the apparatus comprising:
   I/O circuitry to receive an electrocardiographic (ECG) signal and a photoplethysmographic (PPG) signal; and
   blood pressure estimation logic to:
   detect R-wave peaks of the ECG signal;
   identify multiple segments of the PPG signal based on detection of the R-wave peaks of the ECG signal, wherein a segment of the PPG signal comprises a predetermined number of PPG samples and is aligned with a corresponding R-wave peak, wherein the predetermined number of samples per segment is less than a number of samples in the PPG signal between two successive R-wave peaks;
   generate an averaged PPG wave based on the multiple segments of the PPG signal, wherein an element of the averaged PPG wave comprises an average of corresponding elements from the multiple segments of the PPG signal; and
   compute the blood pressure value based on the averaged PPG wave.

2. The apparatus of claim 1, wherein:
   each segment comprises k samples; and
   wherein the blood pressure estimation logic is to: for each i=1 to k, add the ith samples of the multiple segments together and compute an average, wherein the ith element of the averaged PPG wave comprises the computed average of the ith samples of the multiple segments.

3. The apparatus of claim 2, wherein k is less than or equal to a number of samples between successive R-wave peaks of the ECG signal.

4. The apparatus of claim 1, further comprising:
   an ECG sensor to detect the ECG signal, wherein the ECG sensor is coupled with the I/O circuitry and comprises electrodes on a wearable patch.

5. The apparatus of claim 1, further comprising:
   a PPG sensor to detect the PPG signal, wherein the PPG sensor is coupled with the I/O circuitry and comprises a light emitting diode (LED) and a photodiode on a wearable patch.

6. The apparatus of claim 1, further comprising:
   a storage array to store the multiple segments of the PPG signal and the averaged PPG wave.

7. The apparatus of claim 1, wherein the blood pressure estimation logic is to:
   detect a PPG peak in the averaged PPG wave;
   determine pulse transmit time (PTT) based on a time difference between an ECG R-wave peak and the PPG peak of the averaged PPG wave; and
   compute an estimate of the blood pressure value based on the PTT.

8. The apparatus of claim 1, wherein the blood pressure estimation logic is to:
   for a segment of the PPG signal, identify a first sample of the segment in response to detection of a corresponding R-wave peak in the ECG signal.

9. The apparatus of claim 1, wherein the blood pressure estimation logic is to:
   for each segment of the PPG signal, identify a first sample of the segment in response to detection of a corresponding R-wave peak in the ECG signal;
   detect a PPG peak in the averaged PPG wave;
   determine pulse transmit time (PTT) based on a location of the PPG peak of the averaged PPG wave; and
   compute an estimate of the blood pressure value based on the PTT.

10. The apparatus of claim 1, wherein the PPG signal comprises motion artifacts in a same frequency band as PPG peaks of the PPG signal.

11. The apparatus of claim 1, wherein:
    the I/O circuitry is to further transmit the blood pressure value to a remote computing device.

12. A method of determining a blood pressure value, the method comprising:
    receiving an electrocardiographic (ECG) signal and a photoplethysmographic (PPG) signal;
    detecting R-wave peaks in the ECG signal;

identifying multiple segments of the PPG signal based on detection of the R-wave peaks of the ECG signal, wherein a segment of the PPG signal comprises a predetermined number of PPG samples and is aligned with a corresponding R-wave peak, wherein the predetermined number of samples per segment is less than a number of samples in the PPG signal between two successive R-wave peaks;

generating an averaged PPG wave based on the multiple segments of the PPG signal, wherein a given an element of the averaged PPG wave comprises an average of corresponding elements from the multiple segments of the PPG signal; and computing the blood pressure value based on the averaged PPG wave.

13. The method of claim 12, wherein:

each segment comprises k samples; and wherein generating the averaged PPG wave comprises: for each i=1 to k, adding the ith samples of the multiple segments together and computing an average, wherein the ith element of the averaged PPG wave comprises the computed average of the ith samples of the multiple segments.

14. The method of claim 13, wherein k is less than or equal to a number of samples between successive R-wave peaks of the ECG signal.

15. The method of claim 12, wherein identifying the multiple segments of the PPG signal comprises:

for a segment of the PPG signal, identifying a first sample of the segment in response to detection of a corresponding R-wave peak in the ECG signal.

16. The method of claim 12, further comprising:

detecting the ECG signal with an ECG sensor comprising electrodes on a wearable patch.

17. The method of claim 12, further comprising:

detecting the PPG signal with a PPG sensor on a wearable patch, the PPG sensor comprising a light emitting diode (LED) and a photodiode.

18. The method of claim 12, further comprising:

detecting the ECG signal and the PPG signal with sensors on a wearable patch when a user of the wearable patch is in motion.

19. An article of manufacture comprising a computer readable storage medium having content stored thereon which when accessed causes the performance of operations to execute a method comprising:

receiving an electrocardiographic (ECG) signal and a photoplethysmographic (PPG) signal;

detecting R-wave peaks in the ECG signal;

identifying multiple segments of the PPG signal based on detection of the R-wave peaks of the ECG signal, wherein a segment of the PPG signal comprises a predetermined number of PPG samples and is aligned with a corresponding R-wave peak, wherein the predetermined number of samples per segment is less than a number of samples in the PPG signal between two successive R-wave peaks;

generating an averaged PPG wave based on the multiple segments of the PPG signal, wherein an element of the averaged PPG wave comprises an average of corresponding elements from the multiple segments of the PPG signal; and computing a blood pressure value based on the averaged PPG wave.

20. The article of manufacture of claim 19, wherein:

each segment comprises k samples; and wherein generating the averaged PPG wave comprises: for each i=1 to k, adding the ith samples of the multiple segments together and computing an average, wherein the ith element of the averaged PPG wave comprises the computed average of the ith samples of the multiple segments.

* * * * *